(12) United States Patent
Imai et al.

(10) Patent No.: US 10,085,760 B2
(45) Date of Patent: Oct. 2, 2018

(54) MEDICAL DEVICE HAVING A PAIR OF BASKETS

(71) Applicant: TERUMO KABUSHIKI KAISHA, Shibuya-ku, Tokyo (JP)

(72) Inventors: Masaomi Imai, Chuo (JP); Yasuyuki Honma, Matsuda-machi (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 278 days.

(21) Appl. No.: 14/946,141

(22) Filed: Nov. 19, 2015

(65) Prior Publication Data
US 2016/0143652 A1 May 26, 2016

(30) Foreign Application Priority Data

Nov. 21, 2014 (JP) .................................. 2014-236259

(51) Int. Cl.
*A61B 17/221* (2006.01)

(52) U.S. Cl.
CPC .... *A61B 17/221* (2013.01); *A61B 2017/2212* (2013.01)

(58) Field of Classification Search
CPC .... A61B 17/221–2017/2217; A61B 17/32056; A61B 17/12109–17/12122; A61B 17/12022–17/12045; A61B 17/12168–17/12177; A61F 2/013; A61F 2002/016; A61F 2002/018
See application file for complete search history.

(56) References Cited

U.S. PATENT DOCUMENTS

| 4,046,149 A * | 9/1977 | Komiya | A61B 17/221 294/100 |
| 4,612,931 A * | 9/1986 | Dormia | A61B 17/221 606/127 |
| 6,174,318 B1 * | 1/2001 | Bates | A61B 17/221 606/113 |
| 6,348,056 B1 * | 2/2002 | Bates | A61B 17/221 604/22 |
| 6,350,266 B1 * | 2/2002 | White | A61B 17/22031 606/110 |

(Continued)

FOREIGN PATENT DOCUMENTS

| JP | 2008-68102 A | 3/2008 |
| WO | WO 99/16364 A1 | 4/1999 |

*Primary Examiner* — Ryan J Severson
*Assistant Examiner* — Charles Wei
(74) *Attorney, Agent, or Firm* — Buchanan Ingersoll & Rooney PC

(57) ABSTRACT

The medical device disclosed here is configured to remove a plurality of objects at a time from an interior of a living body by restricting the objects from dropping out from an interior of a basket and is capable of treating objects in a body tissues having different structures efficiently with the same device. A treatment portion of a medical device includes an outer basket and an inner basket. A plurality of outer leg portions of the outer basket and a plurality of inner leg portions of the inner basket are arranged so as to be staggered in a circumferential direction. The medical device may be used by being switched between a mode of using only the outer basket and a mode of using both of the outer basket and the inner basket.

15 Claims, 23 Drawing Sheets

(56) References Cited

U.S. PATENT DOCUMENTS

| | | | | |
|---|---|---|---|---|
| 6,383,196 | B1* | 5/2002 | Leslie | A61B 17/221 606/114 |
| 6,706,054 | B2* | 3/2004 | Wessman | A61F 2/01 606/200 |
| 7,094,249 | B1* | 8/2006 | Broome | A61B 17/221 606/200 |
| 8,267,954 | B2* | 9/2012 | Decant, Jr. | A61B 5/02007 606/200 |
| 8,591,540 | B2* | 11/2013 | Boyle | A61F 2/013 606/200 |
| 9,314,248 | B2* | 4/2016 | Molaei | A61B 17/12109 |
| 2002/0151928 | A1* | 10/2002 | Leslie | A61F 2/013 606/200 |
| 2005/0283166 | A1* | 12/2005 | Greenhalgh | A61B 17/221 606/113 |
| 2013/0184739 | A1* | 7/2013 | Brady | A61B 17/221 606/200 |
| 2014/0128905 | A1* | 5/2014 | Molaei | A61B 17/221 606/200 |
| 2015/0250578 | A1* | 9/2015 | Cook | A61F 2/01 606/200 |
| 2016/0331506 | A1* | 11/2016 | Korkuch | A61F 2/013 |

\* cited by examiner

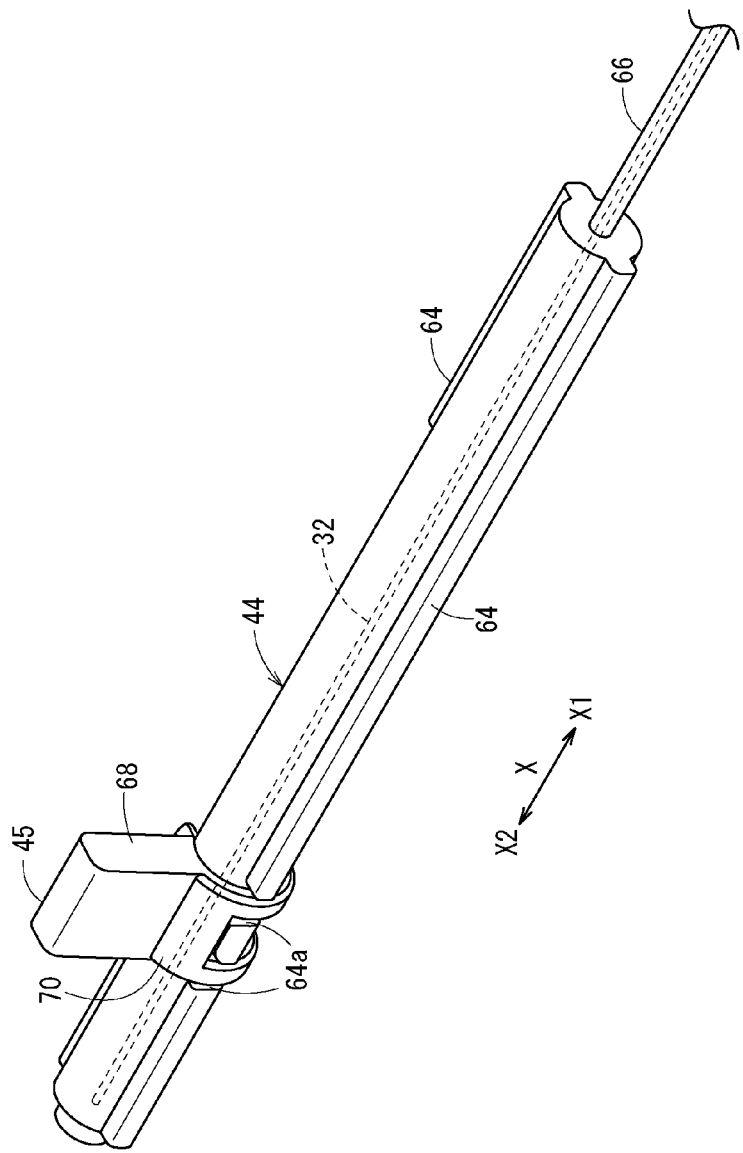

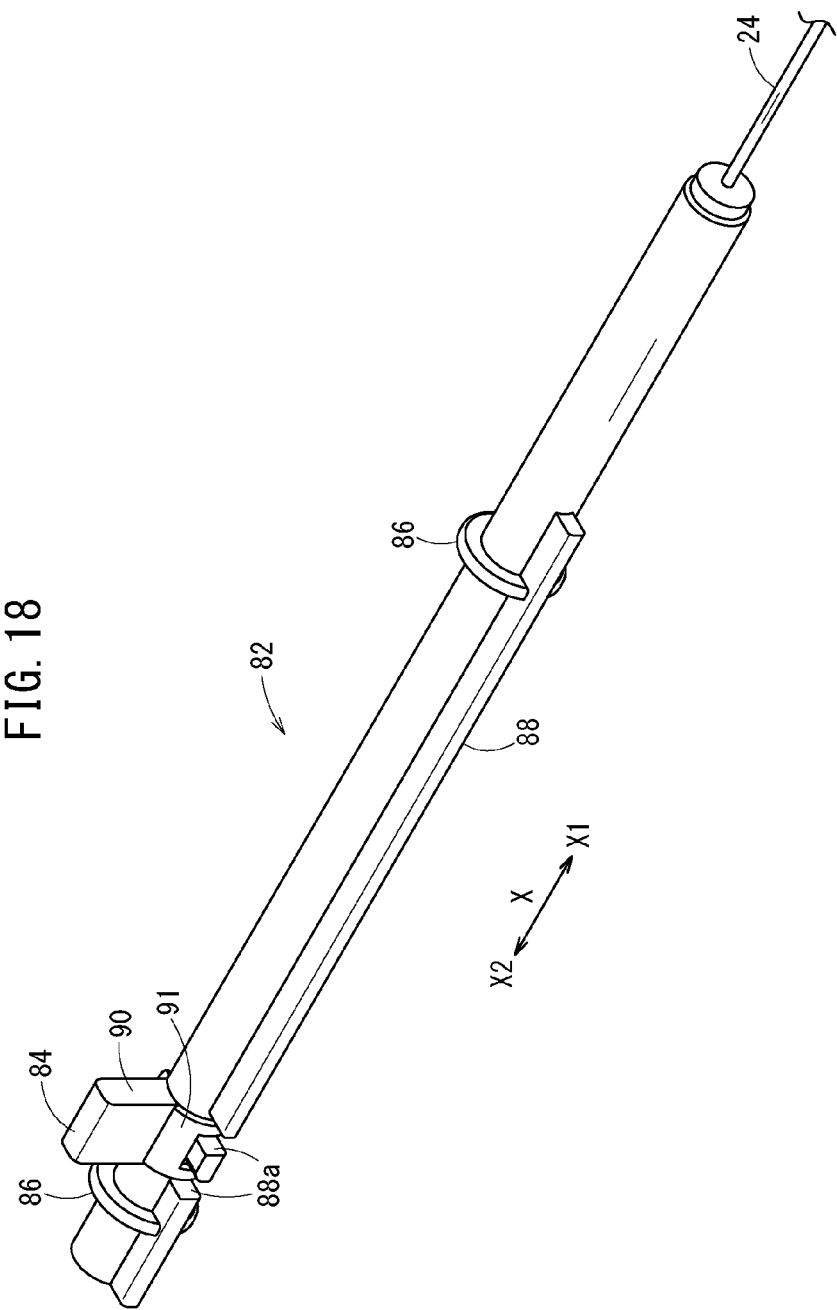

MEDICAL DEVICE HAVING A PAIR OF BASKETS

CROSS-REFERENCES TO RELATED APPLICATIONS

This application claims priority to Japanese Application No. 2014-236259 filed on Nov. 21, 2014, the entire content of which is incorporated herein by reference.

TECHNICAL FIELD

The present invention relates to a medical device used for a medical treatment of in an interior of lumens of a living body.

BACKGROUND DISCUSSION

A medical treatment such as a transurethral ureter lithotripsy or the like is performed for urinary stones generating in a ureter, a renal pelvis, a renal calix and the like (lumens of a living body). In this transurethral ureter lithotripsy, calculus is fractured into a plurality (for example, several tens) of small pieces of calculi by means of a fracturing process such as forceps, shock waves, a laser or the like while viewing calculus with an endoscope (an urethroscope) inserted into a urinary tract, and the plurality of calculi which are fractured and are reduced in size (calculus fragments) are collected with a medical device.

As a medical device configured to collect calculi, for example, as disclosed in Japanese Application Publication Jo. 2008-68102, there is a configuration provided with a basket which can be exposed from a leading end of a sheath. The basket is formed of a plurality of wires. The medical device is inserted into a ureter under an operation of a user such as a medical doctor or the like, the basket is expanded at a location where the calculi exist and catch the calculus fragments into an inside thereof in an expanded state. Subsequently, the user contracts the basket to grasp the calculus fragments, and furthermore, retracts the basket to collect the calculus fragments.

SUMMARY

In the medical device as described above, since gaps between wires which constitute part of the basket are large, when the basket is contracted after the plurality of calculus fragments are caught in the basket, the calculus fragments tend to drop out from the gaps between the wires. Therefore, it is difficult to remove the plurality of calculus fragments at a time, and hence a troublesome operation is required.

In contrast, in order to restrict dropping out of the calculus fragments, forming the basket into a special shape (for example, a net shape) is conceivable. However, although the basket having such a special shape is effective for removing the calculi in the ureter, it does not necessarily have a shape suitable for removing calculi in a renal calix.

In view of such circumstances described above, the medical device disclosed here is configured to remove a plurality of objects at a time from the interior of a living body by restricting the objects from dropping out from the interior of a basket and is configured to treat objects in body tissues having different structures efficiently with the same device.

The medical device disclosed here includes: a handle; an elongated sheath extending from the handle and including a part configured to be inserted into a lumen of a living body; and a treatment portion configured to contract in the sheath and expand in association with exposure outside the sheath. The treatment portion includes: a first basket having a plurality of first leg portions arranged in parallel and spaced apart from one another in a circumferential direction; and a second basket having a plurality of second leg portions arranged in parallel and spaced apart from one another in a the circumferential direction so that the plurality of second leg portions are staggered in the circumferential direction with respect to the plurality of first leg portions. The treatment unit is operable to: i) expand one of the first basket and the second basket in front of the sheath while the other of the first basket and the second basket remains contracted in the sheath; ii) and expand both the first and second baskets in front of the sheath together.

According to the medical device configured in a manner described above, in a case of harvesting a relatively large object, the object can be caught easily and simply into the treatment portion by using only one basket. In contrast, when harvesting a plurality of relatively small objects, dropping out of the plurality of small objects caught in the treatment portion is restricted by using two baskets and reducing gaps in the circumferential direction among the leg portions which constitute the treatment portion. The medical device is capable of selecting one of a mode using one basket and a mode using two baskets which is suitable for collecting the object depending on a location in body tissues from which the object is to be collected. Therefore, according to the medical device of the present invention, an efficient medical treatment can be performed.

In the medical device described above, a configuration in which the handle includes a switching unit configured to be selectively switched between a first switch position and a second switch position, and when an operation to expand the treatment portion is performed in a state in which the switching unit is set at the first switch position, only the one of the first basket and the second basket extends in front of the sheath, and when an operation to expand the treatment portion is performed in a state in which the switching unit is set to the second switch position, both of the first basket and the second basket expand in front of the sheath is also applicable.

In this configuration, setting to one of the mode of using one basket and the mode of using two baskets is achieved simply by switching the switching unit provided on the handle.

In the medical device described above, a configuration in which a first shaft extending from the first basket to the handle along the sheath and a second shaft inserted into the first shaft and extending from the second basket to the handle along the sheath are provided, the handle includes a gripping portion and a sliding member capable of sliding in an axial direction with respect to the gripping portion and being coupled to the sheath, the switching unit restricts a relative movement between the second shaft and the sliding member in the axial direction and allows a relative movement between the second shaft and the gripping portion in the axial direction in a state of being set to the first switch position, and restricts the relative movement between the second shaft and the gripping portion in the axial direction and allows the relative movement between the second shaft and the sliding member in the axial direction in a state of being set to the second switch position is also applicable.

In this configuration, a mechanism configured in such a manner that the second basket is always stored in the sheath irrespective of the position of the sheath and, in contrast, the first basket is exposed from the sheath and is expanded at the time of retraction of the sheath in the state in which the switching unit is set to the first switch position is easily constructed.

In the medical device described above, a configuration in which the handle includes a first shaft base portion arranged in the gripping portion, coupled to the first shaft, and fixed to the gripping portion, and a second shaft base portion arranged in the first shaft base portion, coupled to the second shaft, and being displaceable in the axial direction with respect to the gripping portion, the switching unit is rotatably supported by the second shaft base portion, and protrudes from an outer peripheral surface of the gripping portion, the gripping portion includes a first axial channel configured to allow the relative movement of the switching unit with respect to the gripping portion in the axial direction and a first circumferential channel configured to communicate with the first axial channel and restrict the relative movement of the switching unit with respect to the gripping portion in the axial direction by engaging the switching unit, the sliding member includes a second axial channel configured to allow the relative movement of the switching unit with respect to the sliding member in the axial direction and a second circumferential channel configured to communicate with the second axial channel and restrict the relative movement of the switching unit with respect to the sliding member in the axial direction by engaging the switching unit, and the first shaft base portion includes a third axial channel configured to allow the relative movement of the switching unit with respect to the first shaft base portion in the axial direction and a third circumferential channel communicating with the third axial channel is also applicable.

In this configuration, the switching unit is rotatably supported by the second shaft base portion arranged in the first shaft base portion, and an axial channel and a circumferential channel configured to receive the switching unit are formed in each of the gripping portion, the sliding member, and the first shaft base portion. Therefore, the configuration of switching between a one-basket using mode in which only one basket is used and a two-basket using mode in which both of the first basket and the second basket are used depending on a position of the switching unit is reliably constructed.

In the medical device described above, a configuration in which a first shaft configured to extend from the first basket to the handle along the sheath, and a second shaft inserted into the first shaft and extending from the second basket to the handle along the sheath are provided, the handle includes a gripping portion and a sliding member slidable in an axial direction with respect to the gripping portion and being coupled to the sheath, the switching unit restricts a relative movement between the first shaft and the sliding member in the axial direction and allows a relative movement between the first shaft and the gripping portion in the axial direction in a state of being set to the first switch position, and restricts the relative movement between the first shaft and the gripping portion in the axial direction and allows the relative movement between the first shaft and the sliding member in the axial direction in a state of being set to the second switch position is also applicable.

In this configuration, a mechanism configured in such a manner that the first basket is always stored in the sheath irrespective of the position of the sheath and, in contrast, the second basket is exposed from the sheath and is expanded at the time of retraction of the sheath in the state in which the switching unit is set to the first switch position is easily constructed.

In the medical device described above, a configuration in which the handle includes a first shaft base portion arranged in the gripping portion, coupled to the first shaft, and being displaceable in the axial direction with respect to the gripping portion, the switching unit is rotatably supported by the first shaft base portion, and protrudes from an outer peripheral surface of the gripping portion, the gripping portion includes a first axial channel configured to allow the relative movement of the switching unit with respect to the gripping portion in the axial direction and a first circumferential channel configured to communicate with the first axial channel and restrict the relative movement of the switching unit with respect to the gripping portion in the axial direction by engaging the switching unit, the sliding member includes a second axial channel configured to allow the relative movement of the switching unit with respect to the sliding member in the axial direction and a second circumferential channel configured to communicate with the second axial channel and restrict the relative movement of the switching unit with respect to the sliding member in the axial direction by engaging the switching unit is also applicable.

In this configuration, since the axial channel and the circumferential channel configured to receive the switching unit are formed in each of the gripping portion and the sliding member, the configuration of switching between the one-basket using mode in which only the second basket is used and the two-basket using mode in which both of the first basket and the second basket are used depending on the position of the switching unit is reliably constructed.

In the medical device described above, a configuration in which the first basket includes a ring coupled to a leading end of the plurality of first leg portions, and the second basket is exposed to the front of the sheath through the ring is also applicable.

According to the configuration described above, since the second basket is exposed to the front of the sheath through the ring coupled to the leading end portion of the plurality of first leg portions which constitute the first basket in the case of harvesting the objects by using only the second basket, expansion of the second basket is not hindered by the first basket. Therefore, the second basket can be expanded without problem.

In the medical device described above, a configuration in which the ring is capable of engaging the leading end portion of the sheath, and the sheath pushes the ring toward the leading end when moving forward with respect to the second basket is also applicable.

In this configuration described above, since the sheath pushes the ring of the first basket toward the leading end when the sheath is advanced for storing the second basket into the sheath, such an event that the first basket enters the sheath up to an undesirable position can be effectively prevented.

In the medical device described above, a hollow-cylindrical retaining member configured to retain a plurality of longitudinally extending wires extending from a proximal end portion of the first basket toward a proximal end and a cover tube covering the longitudinally extending wires together with the retaining member and extending in the sheath along the sheath to the handle may be provided.

In this configuration, pushability of the first basket can be desirably secured.

In the medical device described above, a configuration in which a shaft tube fixed to the plurality of longitudinally extending wires extending from the proximal end portion of the first basket toward the proximal end and extending in the sheath along the sheath is provided, and the plurality of longitudinally extending wires may be embedded in the shaft tube is also applicable.

In this configuration, the pushability of the first basket may be desirably secured while restricting an increase in number of components.

In the medical device described above, a configuration in which a plurality of longitudinally extending wires extending from the proximal end portion of the first basket toward the proximal end and extending in the sheath along the sheath are provided, and the plurality of longitudinally extending wires includes a coil portion formed into a close coil shape across a predetermined length along the sheath is also applicable.

In this configuration, the pushability of the first basket can be desirably secured while restricting an increase in number of the components.

In the medical device described above, a configuration in which an operating unit provided on the handle and configured to operate with a finger when expanding or contracting the treatment unit, and a tactile click response generating mechanism configured to generate a click tactile click response at a position where the treatment portion comes to have a predetermined outer diameter when operating the operating unit so as to contract the treatment portion is also applicable.

In this configuration, before performing an operation to pull out the medical device that grips the object with the treatment portion from the access sheath inserted into the lumen of a living body, the fact that the size of the treatment portion is small enough to pass the access sheath can be confirmed in advance.

The medical device of the present invention is capable of removing a plurality of objects at a time from an interior of a living body by restricting objects from dropping out from an interior of a basket and is capable of treating objects in a body tissues having different structures efficiently with the same device.

According to another aspect, a medical device comprises: a handle possessing a distal end; an elongated sheath extending distally from the distal end of the handle, with at least a part of the elongated sheath being configured to be inserted into a lumen of a living body; a first basket comprised of a plurality of first leg portions arranged in parallel in a circumferential direction; and a second basket comprised of a plurality of second leg portions arranged in parallel in a circumferential direction, with each of the second leg portions being positioned between a respective pair of circumferentially adjacent one of the inner leg portions. The first basket is selectively positionable inside the sheath in a contracted state and outside the sheath in an expanded state, with the first basket changing between being positioned inside the sheath and being positioned outside the sheath by virtue of relative movement between the first basket and the sheath. The second basket is selectively positionable inside the sheath in a contracted state and outside the sheath in an expanded state, with the second basket changing between being positioned inside the sheath and being positioned outside the sheath by virtue of relative movement between the first basket and the sheath. An upstanding operating member is operatively connected to the sheath and manually-operable to axially move the sheath, and an upstanding switch is manually-operable to switch between a first switch position in which operation of the operating member axially moves the sheath and the second basket in the proximal direction relative to the first basket so that the first basket is positioned outside the sheath in the expanded state while the second basket is positioned inside the sheath in the contracted state, and a second switch position in which operation of the operating member axially moves the sheath in the proximal direction relative to both the first basket and the second basket so that both the first basket and the second basket are positioned outside the sheath in the expanded state.

Another aspect involves a method comprising: introducing a sheath of a medical device into a lumen of a living body, wherein the medical device includes a first basket comprised of a plurality of first leg portions arranged in parallel in a circumferential direction with a space between circumferentially adjacent pairs of the first leg portion, and a second basket comprised of a plurality of second leg portions arranged in parallel in a circumferential direction with a space between circumferentially adjacent pairs of the first leg portion, wherein each of the second leg portions is positioned between a respective pair of circumferentially adjacent ones of the inner leg portions. The introducing of the sheath into the lumen of the living body comprises introducing the sheath into the lumen of the living body while the first basket is in a contracted state in the sheath and while the second basket is in a contracted state in the sheath. The method also includes relatively axially moving the sheath and the second basket relative to the first basket to expose the first basket outside the sheath so that the first basket expands to an expanded state outside the sheath while the second basket remains inside the sheath in a contracted state, and capturing calculus from the living body inside the first basket while the first basket is outside the sheath and the second basket is inside the sheath in the contracted state.

BRIEF DESCRIPTION OF THE DRAWINGS

FIG. 10 is a perspective view of an inner shaft, the reinforcing tube, the inner shaft base portion, and the switching unit of the medical device illustrated in FIG. 1 viewed from a different angle.

FIG. 18 is a perspective view of an outer shaft, an outer shaft base portion, and a switching unit of the medical device illustrated in FIG. 13.

DETAILED DESCRIPTION

A medical device disclosed here will be described below with reference to the attached drawings which illustrate several embodiments representing examples of the disclosed inventive medical device. In each of the drawings relating to the medical device, an X-direction denotes an axial direction of the medical device and components of the medical device, an X1 direction denotes a direction toward a leading end, and an X2 direction denotes a direction toward a proximal end.

Figure 1:
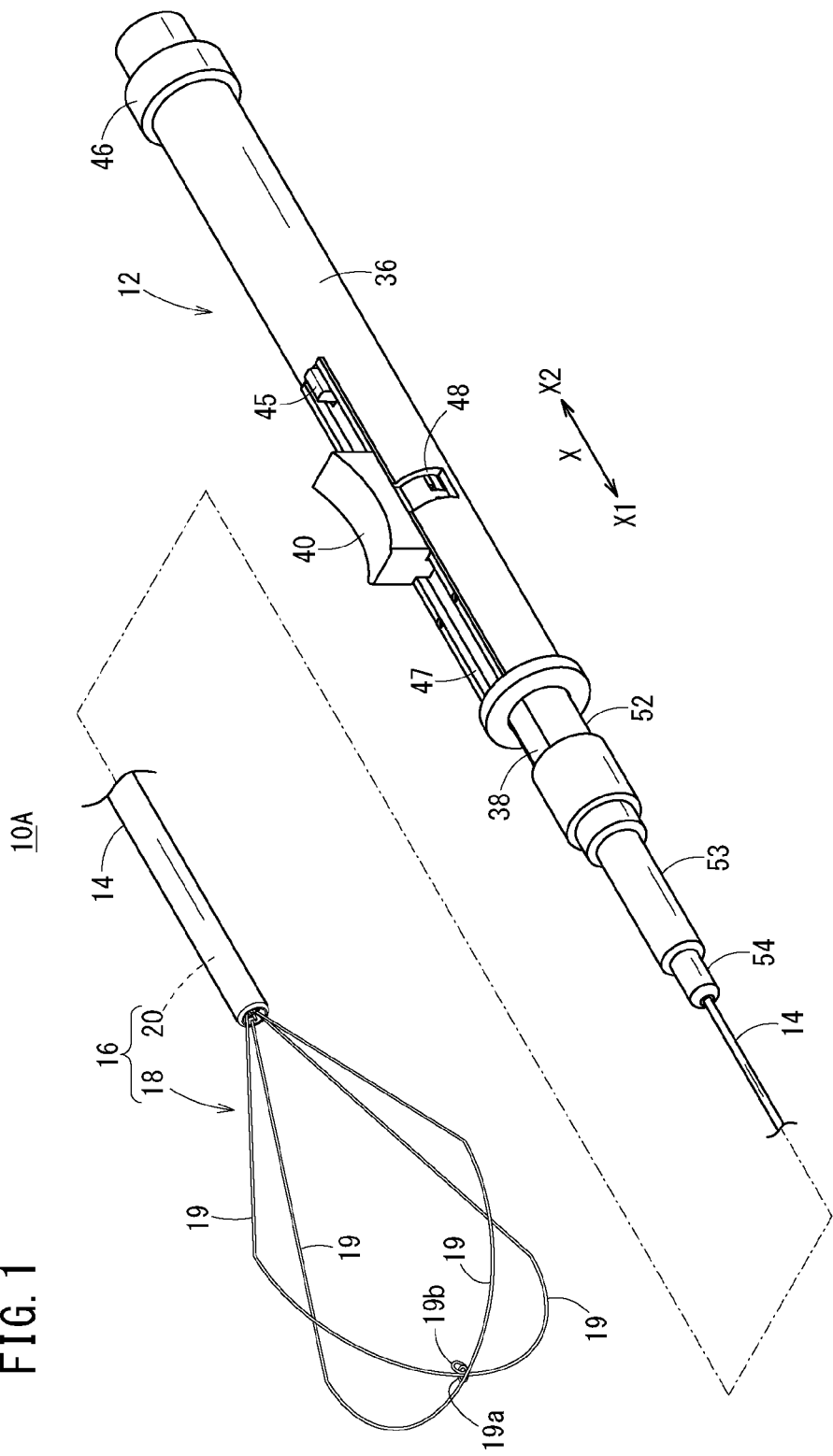
FIG. 1 is a partially omitted perspective view of a medical device (when one basket is expanded) according to a first embodiment of the present invention.
Figure 2:
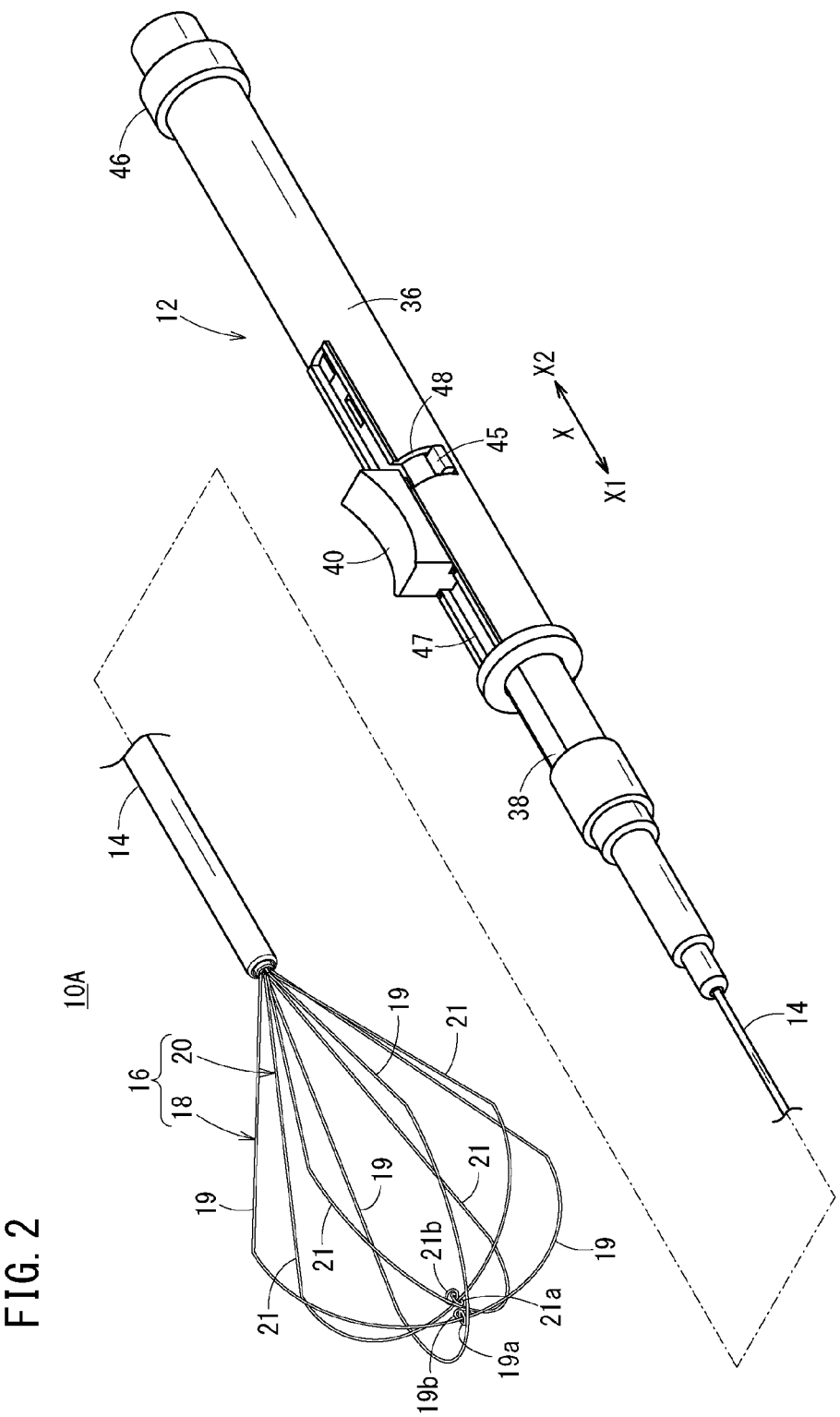
FIG. 2 is a partially omitted perspective view of the medical device (when two baskets are expanded) according to the first embodiment of the present invention.

FIG. 1 is a partially omitted perspective view of a medical device 10A (when one basket is expanded) according to a first embodiment disclosed here. In FIG. 1, for the sake of easy understanding, a leading end portion of the medical device 10A is illustrated in an enlarged scale. FIG. 2 is a partially omitted perspective view of the medical device 10A (when two baskets are expanded). The medical device 10A is configured as medical equipment configured to collect calculi (objects) existing in a urinary system such as a ureter, a renal pelvis, a renal calix and the like, which correspond to lumens of a living body.

The medical device 10A may be applied not only for collecting calculi, but also for medical treatments of various lumens of a living body. Examples of the lumens of a living body to which the medical device 10A is applied include, lumens or other internal organs such as a cardiovascular system, an internal secretion system, a lymph system, a respiratory system, a digestive system and the like in addition to the urinary system. The applicable objects are also the same for a medical device 10B according to a second embodiment, described later.

The medical device 10A includes a handle 12, an elongated sheath 14 extending from the handle 12, and a treatment portion 16 exposed from a leading end portion of the sheath 14 and configured to be expandable. The handle 12 is a mechanical portion gripped by an operator when using the medical device 10A for operating an action of the treatment portion 16. A configuration of the handle 12 will be described in detail later.

The sheath 14 has an axial length sufficient to reach a portion to be treated (locations in a ureter where calculi exist) from an outside of a patient and also possesses adequate flexibility. The sheath 14 is configured to be inserted into the ureter through an interior of a urethroscope (endoscope), and hence is formed to have a diameter significantly smaller than an outer diameter of a portion of the urethroscope to be inserted into the ureter.

The treatment portion 16 is configured to be stored in the sheath 14, is allowed to be exposed at least partly from the leading end portion of the sheath 14, and is configured to be contracted in the sheath 14 and expanded in association with exposure from the sheath 14. Specifically, the treatment portion 16 includes an outer basket 18 (first basket) and an inner basket 20 (second basket).

The medical device 10A is configured to be usable by switching a mode between a one-basket using mode in which only the outer basket 18, out of the outer basket 18 and the inner basket 20, is expanded and contracted and a two-basket using mode in which both the outer basket 18 and the inner basket 20 are expanded and contracted.

In other words, the inner basket 20 is capable of being stored in the sheath 14 when the outer basket 18 is expanded in front of the sheath 14 in the one-basket using mode, and is capable of expanding in front of the sheath 14 together with the outer basket 18 in the two-basket using mode. FIG. 1 illustrates a state in which only the outer basket 18 is expanded, and FIG. 2 illustrates a state in which both of the outer basket 18 and the inner basket 20 are expanded.

The outer basket 18 includes a plurality of (four in this embodiment) linear outer leg portions 19 (first leg portions) disposed in a circumferential direction. Each of the outer leg portions 19 is formed of a resiliently deformable material. Therefore, the outer basket 18 presents a contracted state when stored in the sheath 14, and presents an expanded state when exposed from the leading end of the sheath 14 such that the respective outer leg portions 19 radially expand by their own resilient restoration force.

As illustrated in FIG. 2, the inner basket 20 has a plurality of (four in this embodiment) linear inner leg portions 21 (second leg portions) disposed in the circumferential direction. Each of the inner leg portions 21 is formed of the resiliently deformable material. Therefore, the inner basket 20 presents a contracted state when stored in the sheath 14, and presents an expanded state when exposed from the leading end of the sheath 14 such that the respective inner leg portions 21 radially expand by their own resilient restoration force.

In the case of this embodiment, the four outer leg portions 19 radially expand at angular intervals of 90° in the circumferential direction in front view in a state in which the outer basket 18 is expanded. The four inner leg portions 21 radially expand at angular intervals of 90° in the circumferential direction in front view in a state in which the inner basket 20 is expanded. The plurality of outer leg portions 19 are arranged so as to be staggered in the circumferential direction with respect to the plurality of inner leg portions 21. That is, each of the outer leg portions 19 is positioned between a respective pair of circumferentially adjacent inner leg portions 21. The angular intervals of the circumferentially adjacent outer leg portions 19 and the inner leg portions 21 are 45° in front view.

In the case of this embodiment, the four outer leg portions 19 are formed originally from two wires (i.e., each wire forms two of the leg portions 19), and, in the same manner, the four inner leg portions 21 are formed originally from two wires (i.e., each wire forms two of the leg portions 21).

In other words, the two outer leg portions 19 located on sides opposite to each other with reference to an axial line (central axis) of the sheath 14 are formed originally from one wire by bending the wire into a ring shaped member at an intermediate portion of the wire, and the outer basket 18 is formed by arranging two of the ring-shaped members at an angle of 90° shifted in front view. Therefore, the outer basket 18 presents a cross shape in front view.

Two small rings 19a, 19b are provided at a leading end of the outer basket 18. The ring 19a, which is one of the rings, is fixed to one of the wires and the other wire is inserted through this one ring 19a. The ring 19b, which is the other ring, is fixed to the other wire and the one of the wires is inserted through this other ring 19b. Accordingly, misalignment of coupling positions of the wires with respect to each other is prevented.

In the same manner, the two inner leg portions 21 located on sides opposite to each other with reference to the axial line of the sheath 14 are formed originally from one wire by bending the wire into a ring shaped member at an intermediate portion of the wire, and the inner basket 20 is formed by arranging two of the ring-shaped members at an angle of 90° shifted in front view. Therefore, the inner basket 20 presents a cross shape in front view.

Two small rings 21a, 21b are provided at the leading end of the inner basket 20. The ring 21a, which is one of the rings, is fixed to one of the wires and the other wire is inserted through this one ring 21a. The ring 21b, which is the other ring, is fixed to the other wire and the one of the wires is inserted through this other ring 21b. Accordingly, a misalignment of the coupling positions of the wires with respect to each other is prevented.

The outer basket 18 and the inner basket 20 need to expand by themselves, by virtue of a resilient restoration force, in association with the transition from a state of being stored in the sheath 14 to a state of being exposed to the outside of the sheath 14. Therefore, examples of materials of the outer leg portions 19 and the inner leg portions 21 include, for example, a pseudoelastic alloy (including superelastic alloy) such as Ni—Ti system alloy, shape-memory alloy, and the like.

Figure 3:
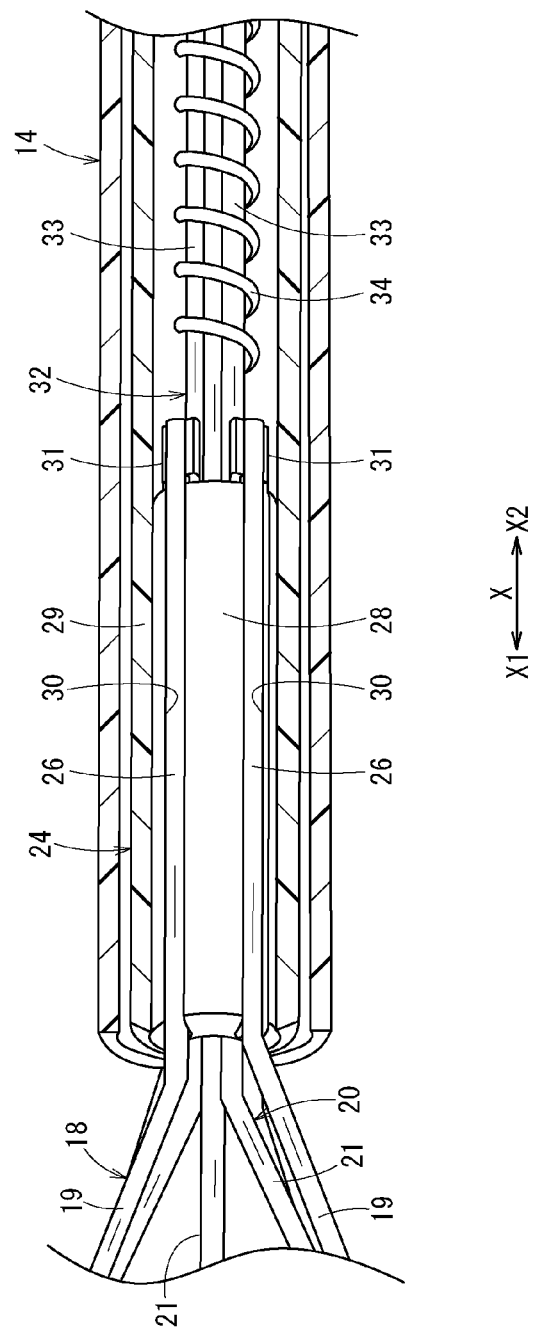
FIG. 3 is a partial cross-sectional side view of a periphery of a leading end portion of an outer shaft of the medical device illustrated in FIG. 1.

FIG. 3 is a partially cross-sectional side view of a proximal end side of the outer basket 18 and the inner basket 20 in a state in which the outer basket 18 and the inner basket 20 are exposed from the leading end of the sheath 14 and are expanded. As illustrated in FIG. 3, an outer shaft 24 (first shaft) extending from the outer basket 18 to the handle 12 along the sheath 14 is inserted into the sheath 14.

In the case of this embodiment, the outer shaft 24 includes a plurality of longitudinally extending wires 26 extending from the respective proximal end portions of the plurality of outer leg portions 19, which constitute part of the outer basket 18, toward the proximal end of the longitudinally extending wires 26 by a predetermined length, a hollow cylindrical retaining member 28 configured to retain the plurality of longitudinally extending wires 26, and a cover tube 29 covering the plurality of longitudinally extending wires 26 and the retaining member 28 and extending to the handle 12. The retaining member 28 is fixed to the cover tube 29.

In the case of this embodiment, the respective longitudinally extending wires 26 are the same members continuing from the respective outer leg portions 19. A plurality of retaining grooves 30 extending in the axial direction are formed on an outer peripheral portion of the retaining member 28 at spaced-apart intervals in the circumferential direction. The numbers of the retaining grooves 30 and the longitudinally extending wires 26 are the same. The respective longitudinally extending wires 26 are retained in the respective retaining grooves 30. In addition, protruding portions 31 which engage a proximal outer peripheral portion of the retaining member 28 are formed at proximal end portions of the respective longitudinally extending wires 26, so that the longitudinally extending wires 26 are prevented from coming off from the retaining member 28 toward the leading end.

An inner shaft 32 extending from the inner basket 20 to the handle 12 along the sheath 14 is inserted into the outer shaft 24. In the case of this embodiment, the inner shaft 32 includes a plurality of longitudinally extending wires 33 extending from the respective proximal end portions of the plurality of inner leg portions 21, which constitute part of the inner basket 20, toward the proximal end and extending to the handle 12. The plurality of longitudinally extending wires 33 are inserted into (i.e., pass through) the retaining member 28.

A binding wire 34 is wound around the plurality of longitudinally extending wires 33 in a helical manner on a proximal end side of the retaining member 28, and the plurality of longitudinally extending wires 33 are bound together by the binding wire 34. Accordingly, pushability of the inner shaft 32 and the inner basket 20 is secured.

Figure 4:
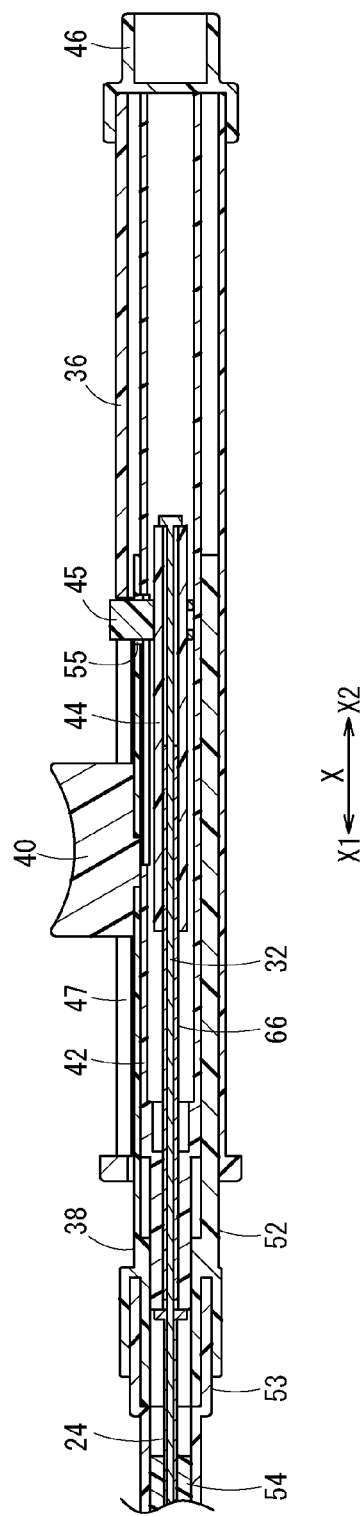
FIG. 4 is a vertical cross-sectional view of a handle of the medical device illustrated in FIG. 1.

FIG. 4 is a vertical cross-sectional view of the handle 12. The handle 12 includes a gripping portion 36 that the operator grips, a sliding member 38 being slidable in the axial direction with respect to the gripping portion 36, an operating unit 40 (operating element) provided on the sliding member 38, an outer shaft base portion 42 provided in the gripping portion 36, an inner shaft base portion 44 provided in the outer shaft base portion 42, and a switching unit 45 (switch) rotatably supported by the inner shaft base portion 44.

Figure 6:
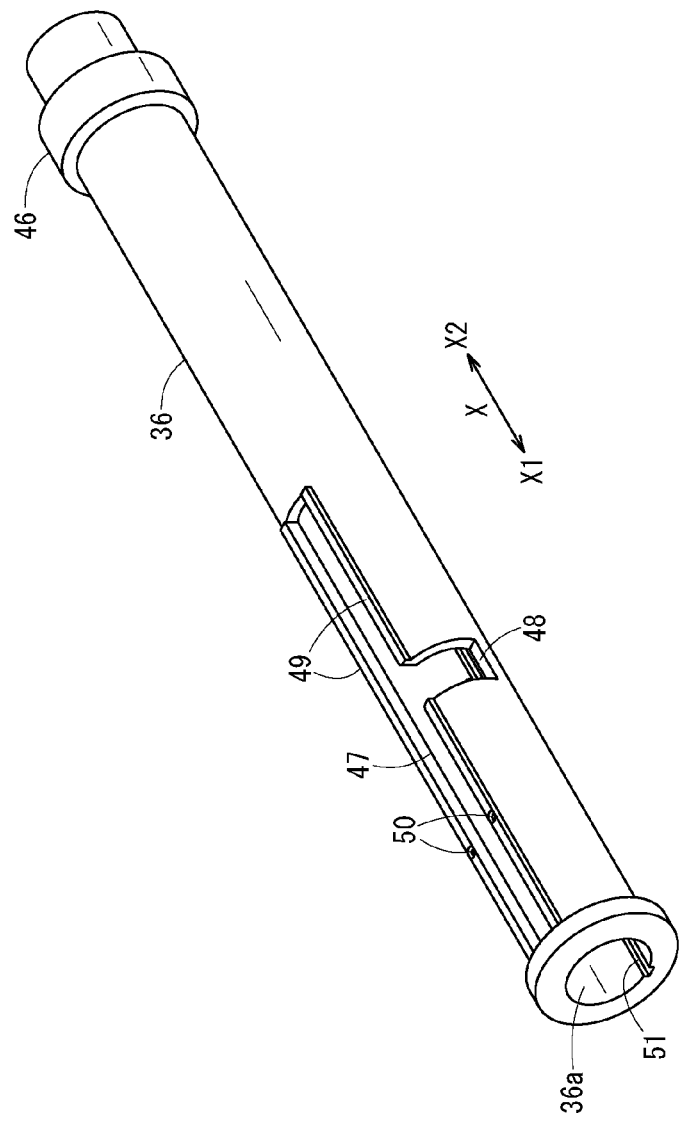
FIG. 6 is a perspective view of a gripping portion and a lid member of the medical device illustrated in FIG. 1.

As illustrated in FIG. 6, the gripping portion 36 possesses a hollow cylindrical shape having an inner cavity 36a penetrating through the gripping portion 36 in the axial direction, and the proximal end portion of the gripping portion 36 is closed by a lid member 46. An elongated hole 47 (first axial channel) extending in the axial direction and a notch shaped engaging groove 48 (first circumferential channel) extending in the circumferential direction from an intermediate portion of the elongated hole 47 are formed on an upper portion of the gripping portion 36. As illustrated in FIG. 4, the elongated hole 47 receives the operating unit 40 and the switching unit 45, and allows their movement in the axial direction. In FIG. 6, the engaging groove 48 ends at a side portion of the gripping portion 36, and is configured to receive the switching unit 45 and engaging the switching unit 45.

As illustrated in FIG. 6, protruding guiding seats 49 are located at both sides of the elongated hole 47 on the outer peripheral surface of the gripping portion 36 so as to extend in the axial direction along the elongated hole 47. Engaging depressions 50 are provided on upper surfaces of the respective guiding seats 49 at positions between the leading end of the elongated hole 47 and the engaging groove 48. A rotation preventing groove 51 extending in the axial direction is provided on an inner peripheral surface of the gripping portion 36.

As illustrated in FIG. 4, the sliding member 38 includes a sliding cylinder 52 supported by the gripping portion 36 so as to be slidable, a first kink-resistant tube 53 fixed to the leading end portion of the sliding cylinder 52, and a second kink-resistant tube 54 fixed to a leading end portion of the first kink-resistant tube 53.

Figure 7:
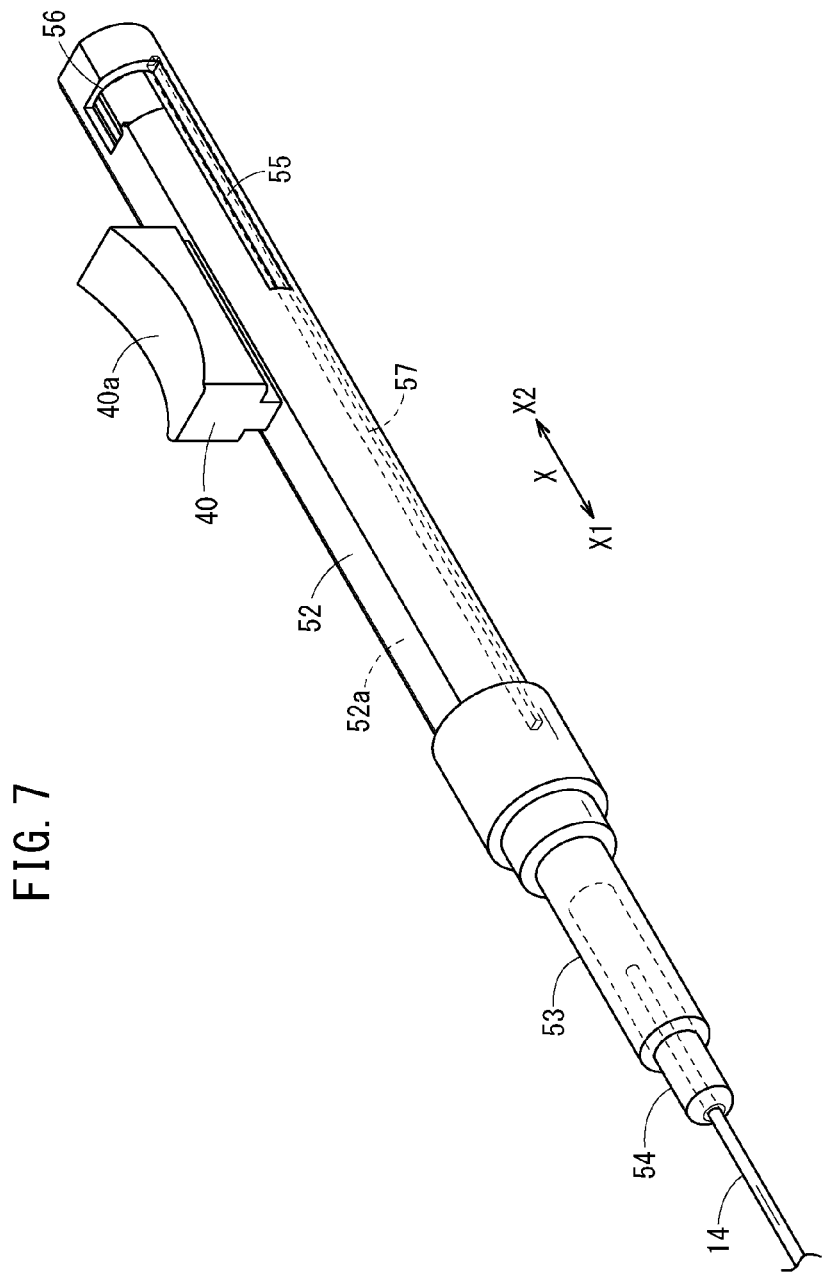
FIG. 7 is a perspective view of a sheath, a sliding member, and an operating unit of the medical device illustrated in FIG. 1.

As illustrated in FIG. 7, the sliding cylinder 52 possesses a hollow cylindrical shape having an inner cavity 52a penetrating in the axial direction, and includes an elongated hole 55 (second axial channel) extending in the axial direction and a notch shaped engaging groove 56 (second circumferential channel) extending from the proximal end portion of the elongated hole 55 in the circumferential direction on a side portion of the elongated hole 55. The engaging groove 56 ends at an upper portion of the sliding cylinder 52. The elongated hole 55 receives the switching unit 45, and allows the movement of the sliding cylinder 52 in the axial direction with respect to the switching unit 45 (see FIG. 12B). The engaging groove 56 receives the switching unit 45, and is configured to engage the switching unit 45. The circumferential direction in which the engaging groove 56 of the sliding cylinder 52 extends from the elongated hole 55 and the circumferential direction in which the engaging groove 48 of the gripping portion 36 extends from the elongated hole 47 are opposite directions to each other.

In FIG. 7, a rotation preventing rib 57 extending in the axial direction is located on the outer peripheral surface of the sliding cylinder 52. By virtue of the rotation preventing rib 57 being inserted into or positioned in the rotation preventing groove 51 provided on the gripping portion 36 (FIG. 6), rotation of the sliding cylinder 52 with respect to the gripping portion 36 is prevented.

The first kink-resistant tube 53 and the second kink-resistant tube 54 are members interposed between the sheath 14 and the sliding cylinder 52 for restricting the sheath 14 from bending when the sheath 14 is pushed in during the usage of the medical device 10A. The second kink-resistant tube 54 possesses a smaller outer diameter than the first kink-resistant tube 53, and the proximal end portion of the sheath 14 is fixed to the inner side of the second kink-resistant tube 54.

The operating unit 40 is fixed to the upper portion of the sliding cylinder 52, and protrudes upward from the gripping portion 36 via the elongated hole 47 of the gripping portion 36 (see FIG. 4). A finger placing surface 40a depressed in an arc shape toward the sliding cylinder 52 is provided on the upper surface of the operating unit 40, whereby pushing and pulling operations of the operating unit 40 by the user are facilitated.

In the medical device 10A, in a state in which the operating unit 40 is located on the leading end side of the elongated hole 47 on the gripping portion 36 (FIG. 11A and FIG. 12A), the sheath 14 coupled to the operating unit 40 via the sliding member 38 is located at an advanced position, so that both of the outer basket 18 and the inner basket 20 are stored in the sheath 14 and present a contracted state. In contrast, when the operating unit 40 is moved toward the proximal end with respect to the gripping portion 36 from this state, the sheath 14 coupled to the operating unit 40 via the sliding member 38 retracts or moved rearwardly in the proximal direction. In association with the retraction of the sheath 14, the treatment portion 16 expands in front of the sheath 14. At this time, whether only the outer basket 18 expands or both of the outer basket 18 and the inner basket 20 expand is determined by a setting state (switching position) of the switching unit 45.

Figure 5:
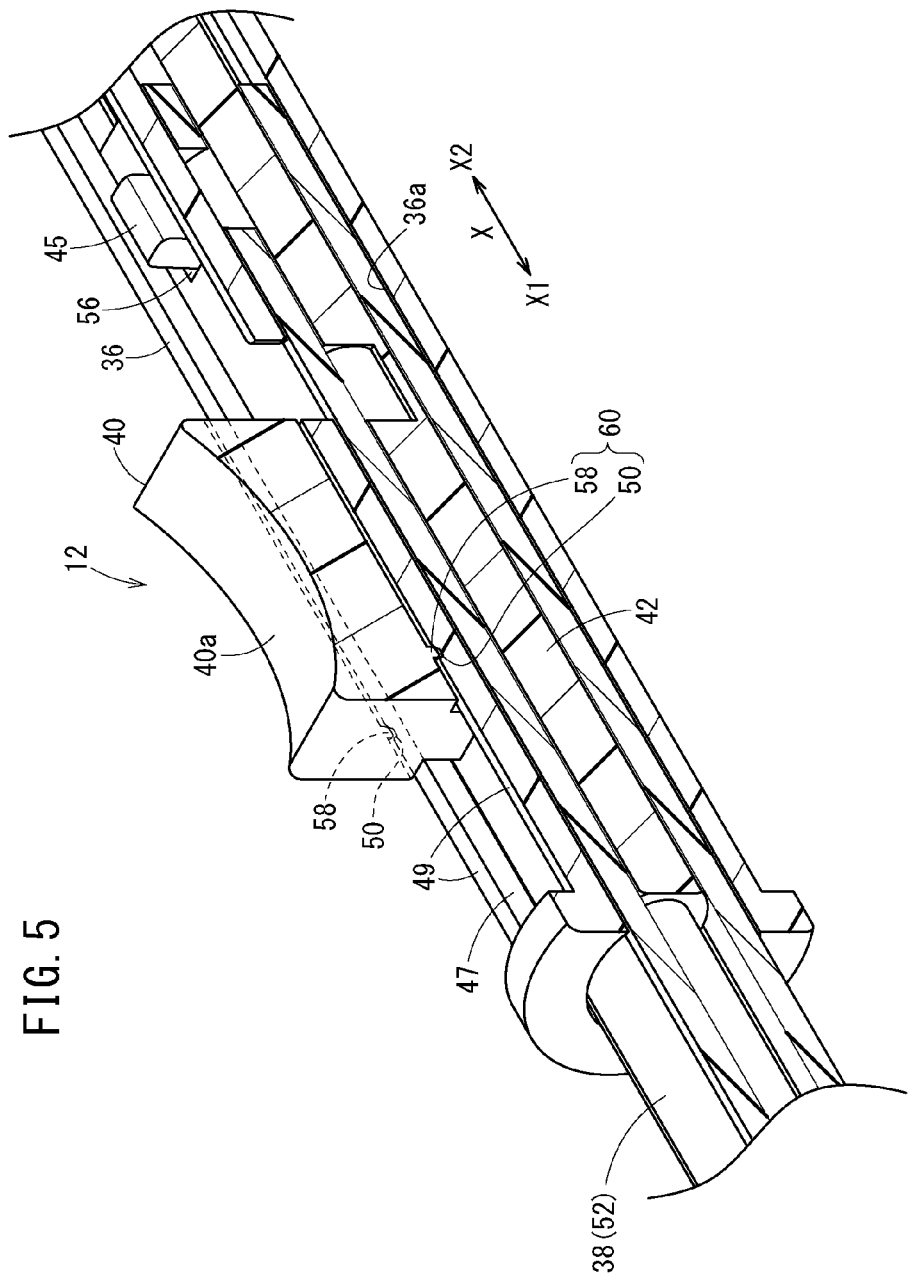
FIG. 5 is a perspective cross-sectional view of the handle for explaining a tactile click response generating mechanism of the medical device illustrated in FIG. 1.

As illustrated in FIG. 5, engaging projections 58 projecting toward the guiding seats 49 side are formed at portions of the operating unit 40 facing the guiding seats 49. The engaging projections 58 are configured to engage depressions 50 formed on the guiding seats 49. The engaging projections 58 and the engaging depressions 50 constitute tactile click response generating mechanisms 60 that generate a tactile click response at a position where the treatment portion 16 comes to have a predetermined outer diameter when operating the operating unit 40 so as to contract the treatment portion 16.

In order to pull out the medical device 10A that grips calculus fragments with the treatment portion 16 from the ureteral access sheath having a sizes of 12 Fr, an outer diameter of the treatment portion 16 that grips the calculus fragments needs to be smaller than 4 mm. Therefore, in the medical device 10A, the positional relationship between the engaging projections 58 and the engaging depressions 50 is set so that a tactile click response is generated at a position where the outer diameter of the treatment portion 16 is smaller than 4 mm in order to confirm in advance the fact that the size of the treatment portion 16 is in a state of being capable of passing through (sized to pass through) the ureteral access sheath before an operation of pulling out the medical device 10A that grips the calculus fragments with the treatment portion 16 from the ureteral access sheath is performed.

In other words, in the case where a tactile click response is generated by the engagement between the engaging projections 58 and the engaging depressions 50 when pushing the operating unit 40 toward the leading end (distal or forward end) in order to grip the calculus fragments, if the operating unit 40 is located on the leading end side with respect to the position where the tactile click response is generated, it means that the treatment portion 16 that grips the calculus fragments can pass through the ureteral access sheath. Accordingly, the medical device 10A can efficiently perform the operation of pulling out the medical device 10A from the ureteral access sheath.

Figure 8:
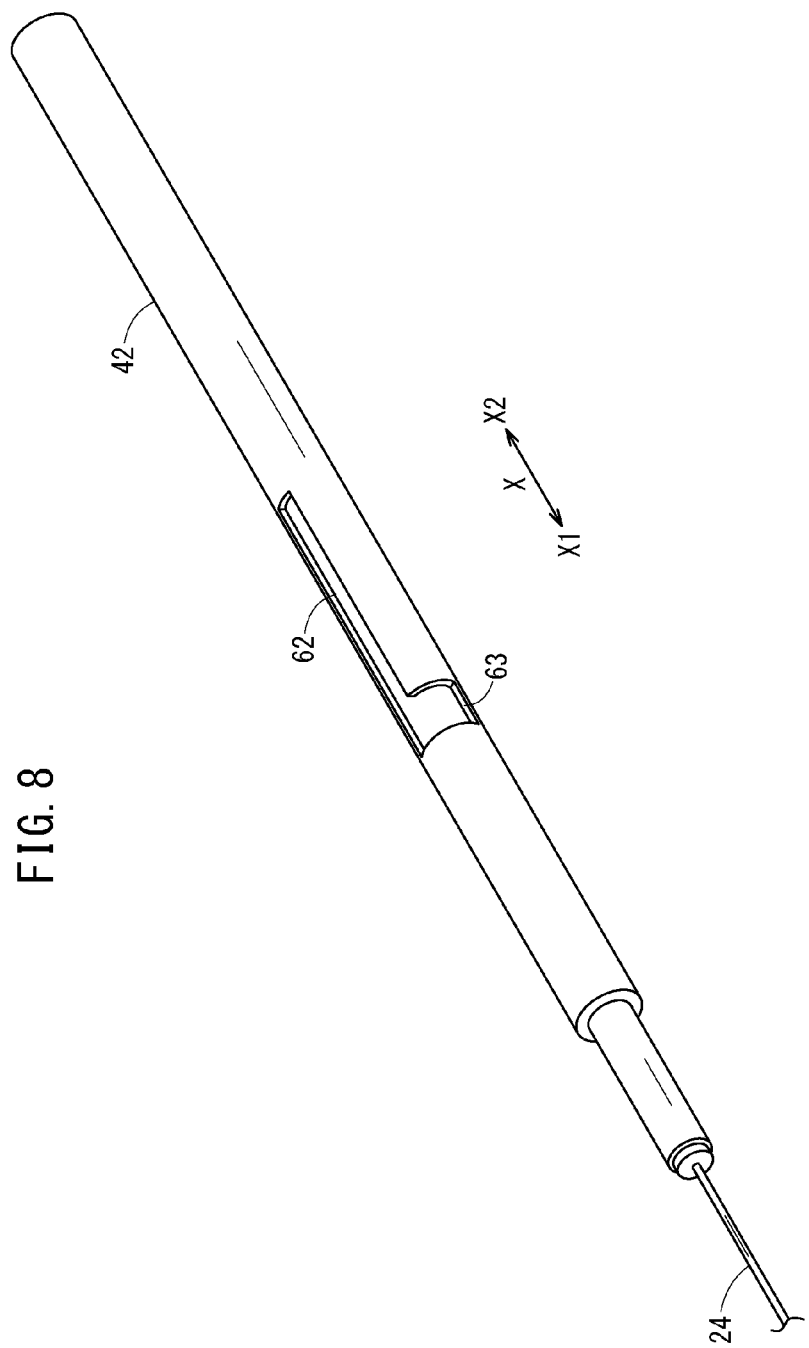
FIG. 8 is a perspective view of the outer shaft and an outer shaft base portion of the medical device illustrated in FIG. 1.

As illustrated in FIG. 8, the outer shaft base portion 42 possesses a hollow cylindrical shape. The outer shaft 24 is fixed to the leading end of the outer shaft base portion 42. The proximal end portion of the outer shaft base portion 42 is fixed to the lid member 46 (FIG. 4). Therefore, the outer shaft base portion 42 is fixed to the gripping portion 36 via the lid member 46, and so rotation and axial displacement of the outer shaft base portion 42 with respect to the gripping portion 36 is restricted.

An elongated hole 62 (third axial channel) extending in the axial direction and a notch shaped engaging groove 63

(third circumferential channel) extending in the circumferential direction from a leading end portion of the elongated hole 62 are formed on an upper portion of the outer shaft base portion 42. The elongated hole 62 receives the switching unit 45, and allows the movement of the switching unit 45 in the axial direction of the switching unit 45. The engaging groove 63 receives the switching unit 45, and is configured to engage the switching unit 45. The circumferential direction in which the engaging groove 63 of the outer shaft base portion 42 extends from the elongated hole 62 and the circumferential direction in which the engaging groove 48 of the gripping portion 36 extends from the elongated hole 47 are the same direction.

In FIG. 4, the inner shaft base portion 44 is slidable with respect to the outer shaft base portion 42 in the axial direction inside the outer shaft base portion 42. The inner shaft 32 is fixed to the inner shaft base portion 44. In the case of this embodiment, the inner shaft 32 is inserted into the inner shaft base portion 44, and is fixed to the inner shaft base portion 44 at the proximal end portion of the inner shaft base portion 44.

Figure 9:
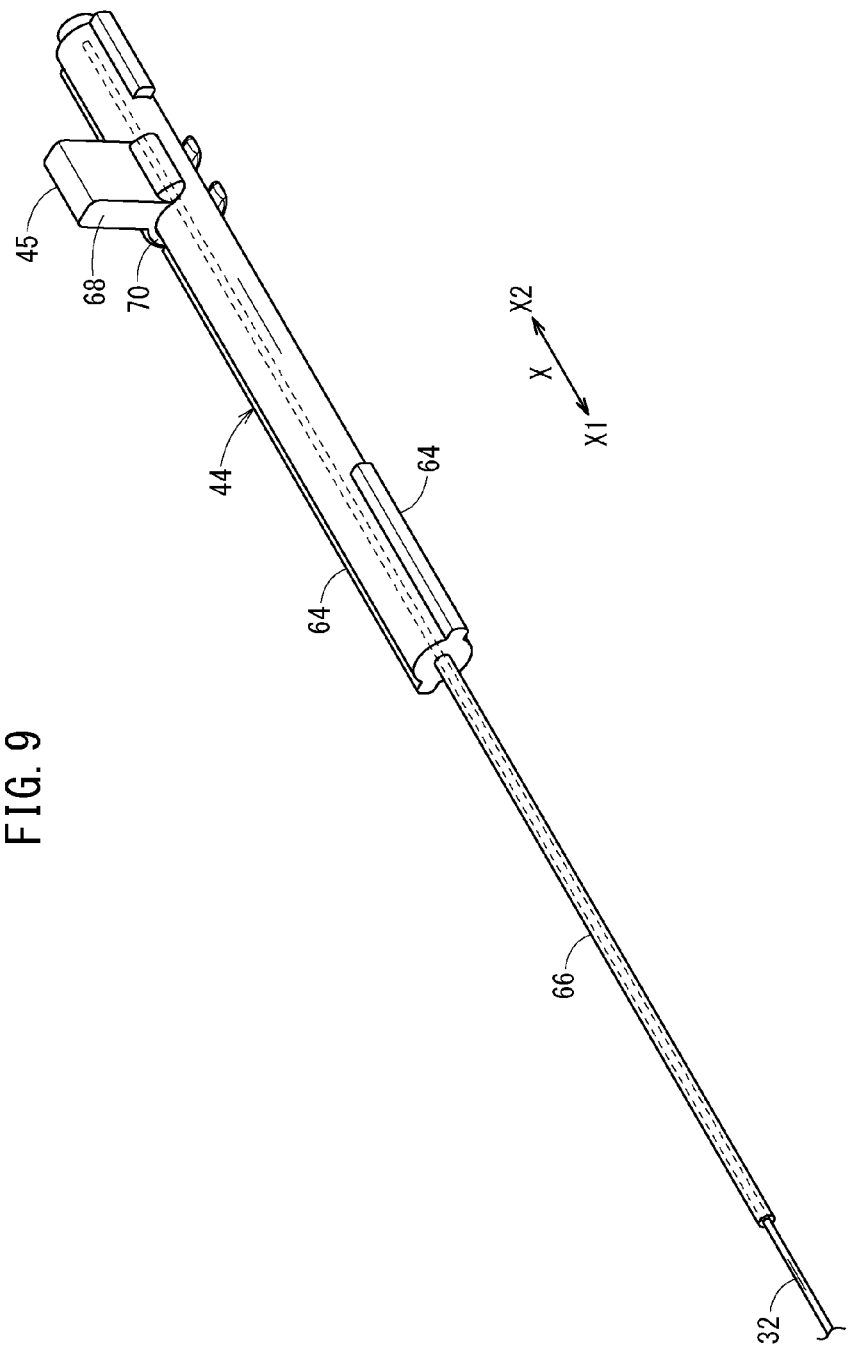
FIG. 9 is a perspective view of an inner shaft, and a reinforcing tube, an inner shaft base portion, and a switching unit of the medical device illustrated in FIG. 1.

As illustrated in FIG. 9 and FIG. 10, ribs 64 which prevent radial rattling with respect to the outer shaft base portion 42 are provided on an outer peripheral portion of the inner shaft base portion 44. In the case where the inner shaft base portion 44 is located at an advanced position with respect to the outer shaft base portion 42, the leading end portions of the ribs 64 of the inner shaft base portion 44 enter grooves provided on an inner peripheral portion of the outer shaft base portion 42 on the leading end side, so that a rotation of the inner shaft base portion 44 with respect to the outer shaft base portion 42 is prevented.

A reinforcing tube 66 configured to reinforce the inner shaft 32 is fixed to the inner shaft base portion 44. The reinforcing tube 66 protrudes from the inner shaft base portion 44 toward the leading end, and partly covers the inner shaft 32 within the outer shaft base portion 42.

The switching unit 45 is configured to be selectively switched between the first switch position (see FIG. 11A) at which only the first basket is expanded in front of the sheath 14 in association with an expanding operation of the treatment portion 16 and the second switch position (see FIG. 12A) at which both the outer basket 18 and the inner basket 20 are expanded in front of the sheath 14 in association with an expanding operation of the treatment portion 16. The switching unit 45 engages the sliding member 38 at the first switch position and engages the gripping portion 36 at the second switch position.

In the case of this embodiment, the switching unit 45 is attached to the inner shaft base portion 44 so as to be rotatable about an axial line (central axis) of the inner shaft base portion 44, and protrudes outward from the outer peripheral surface of the gripping portion 36. Specifically, as illustrated in FIG. 9 and FIG. 10, the switching unit 45 includes an operation tab 68 to which a finger is placed, and a connecting portion 70 configured to be rotatably connected to or mounted on the inner shaft base portion 44. The connecting portion 70 is a C-shape connecting element, and partly surrounds the inner shaft base portion 44 so as to traverse portions 64a formed by notching the ribs 64 (see FIG. 10). Accordingly, the switching unit 45 is prevented from moving in the axial direction and is allowed to rotate with respect to the inner shaft base portion 44.

The medical device 10A according to this embodiment is configured as described above, and an operation of the medical device 10A will be described below.

The medical device 10A is used, for example, for transurethral ureter lithotripsy. In the transurethral ureter lithotripsy, an operator anesthetizing a patient and then inserts the ureteral access sheath into his/her ureter. Subsequently, a urethroscope (endoscope) is inserted into the ureteral access sheath to confirm a calculus to be collected. Subsequently, a laser fiber is inserted into a working channel (insertion lumen) of the urethroscope to fracture the calculus. At this time, the calculus is fractured into, for example, several to several tens of calculus fragments. The calculus may be fractured by other calculus fracturing devices (forceps, electrohydraulic shock wave lithotripsy apparatus, and the like) instead of the laser fiber.

Subsequently, the laser fiber is pulled out from the urethroscope and the medical device 10A is inserted into a working channel of the urethroscope instead. At the time of insertion into the urethroscope, the medical device 10A is prepared in advance to be in a state in which the outer basket 18 and the inner basket 20 are contracted inside the sheath 14 (contracted position of the treatment portion) by positioning the operating unit 40 on the leading end side of the elongated hole 47 of the gripping portion 36 and setting the sheath 14 at an advanced position. The medical device 10A is then advanced into the ureter, and the leading end portion of the medical device 10A is moved to reach a position in the vicinity of the calculus fragments.

Figure 11A:
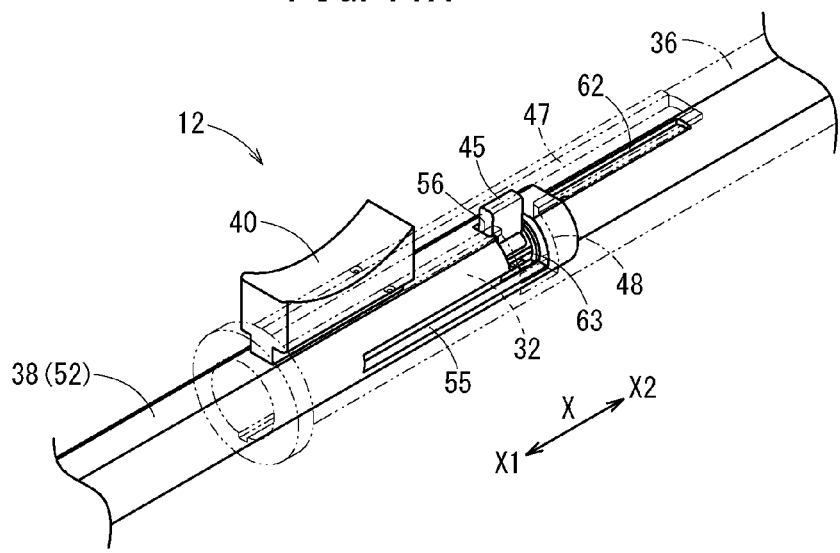
FIG. 11A is a perspective view of the handle in the medical device illustrated in FIG. 1 when the switching unit is set at a first switch position and the operating unit is at an advanced position.

Here, in the case of collecting (removing) large calculus fragments, the switching unit 45 is set to the first switch position as illustrated in FIG. 11A. In the state in which the switching unit 45 is set to the first switch position, the switching unit 45 is arranged in the engaging groove 56 of the sliding cylinder 52, and is separated from the engaging groove 48 of the gripping portion 36. Therefore, a relative movement between the inner shaft 32 and the sliding member 38 in the axial direction is restricted, and the relative movement between the inner shaft 32 and the gripping portion 36 in the axial direction is allowed.

Figure 11B:
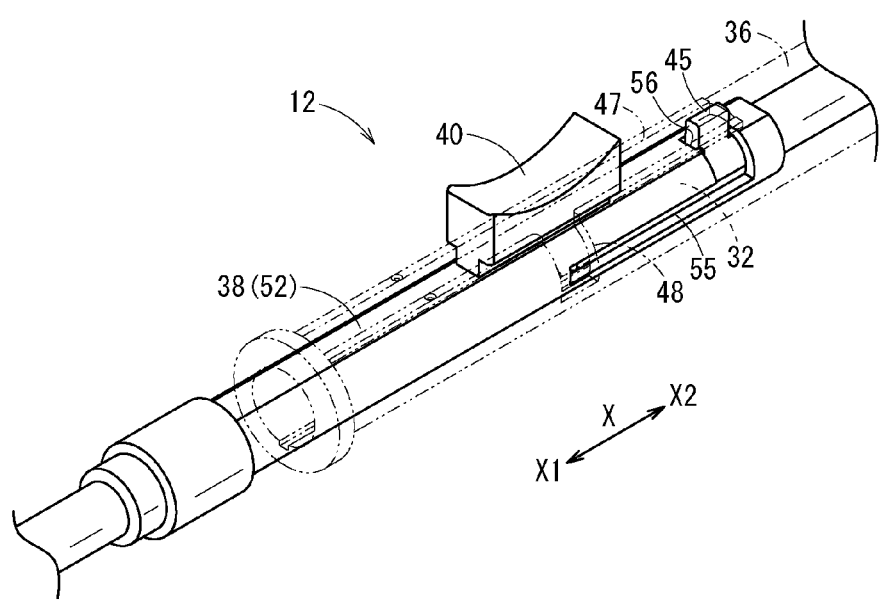
FIG. 11B is a perspective view of the handle in the medical device illustrated in FIG. 1 when the switching unit is set at the first switch position and the operating unit is at a retracted position.

Therefore, if the operating unit 40 is operated by a finger and is retracted toward the proximal end, the sheath 14 and the inner basket 20 are integrally retracted with respect to the outer basket 18 as illustrated in FIG. 11B. At this time, as illustrated in FIG. 1, the outer basket 18 is expanded in association with exposure from the sheath 14, while the inner basket 20 which is retracted together with the sheath 14 remains stored in the sheath 14 (expanded position of the treatment portion). Consequently, only the outer basket 18 is expanded.

Then, the medical device 10A is operated to catch the calculus fragments into the outer basket 18 via gaps among the outer leg portions 19. In this case, the basket to be used is only the outer basket 18, and since the gaps among the leg portions are relatively large, large calculus fragments can be caught easily. When the calculus fragments are caught in the outer basket 18, the operator then pushes the operating unit 40 toward the leading end, and the sheath 14 is advanced with respect to the outer basket 18. Accordingly, the outer basket 18 starts to reduce the diameter, and grasps the calculus fragments. Subsequently, in the state of grasping the calculus fragments with the outer basket 18, the medical device 10A is pulled out from the ureteral access sheath together with the urethroscope.

Figure 12A:
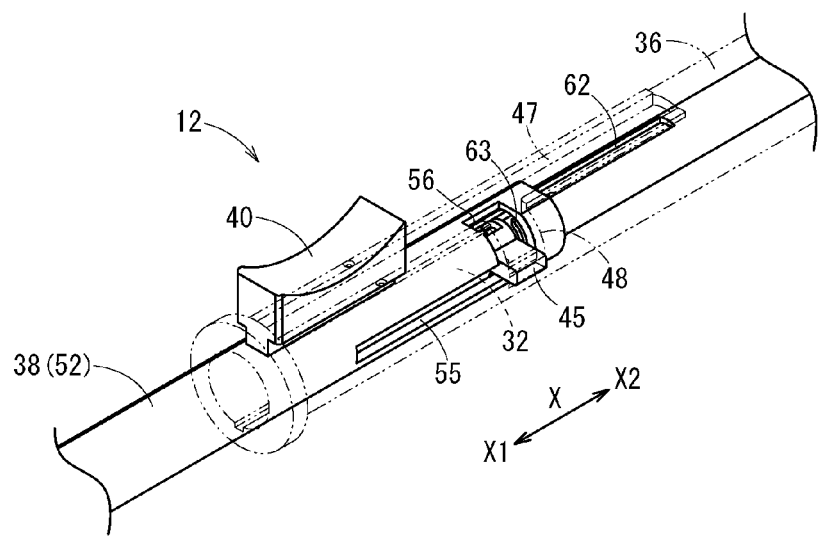
FIG. 12A is a perspective view of the handle in the medical device illustrated in FIG. 1 when the switching unit is set at a second switch position and the operating unit is at an advanced position.

In contrast, in the case of collecting (removing) a plurality of small calculus fragments, the switching unit 45 is set to the second switch position as illustrated in FIG. 12A. In the state in which the switching unit 45 is set to the second switch position, the switching unit 45 is separated from the engaging groove 56 of the sliding cylinder 52, and is positioned in the engaging groove 48 of the gripping portion 36. Therefore, a relative movement between the inner shaft 32 and the sliding member 38 in the axial direction is allowed, and the relative movement between the inner shaft 32 and the gripping portion 36 in the axial direction is restricted.

Figure 12B:
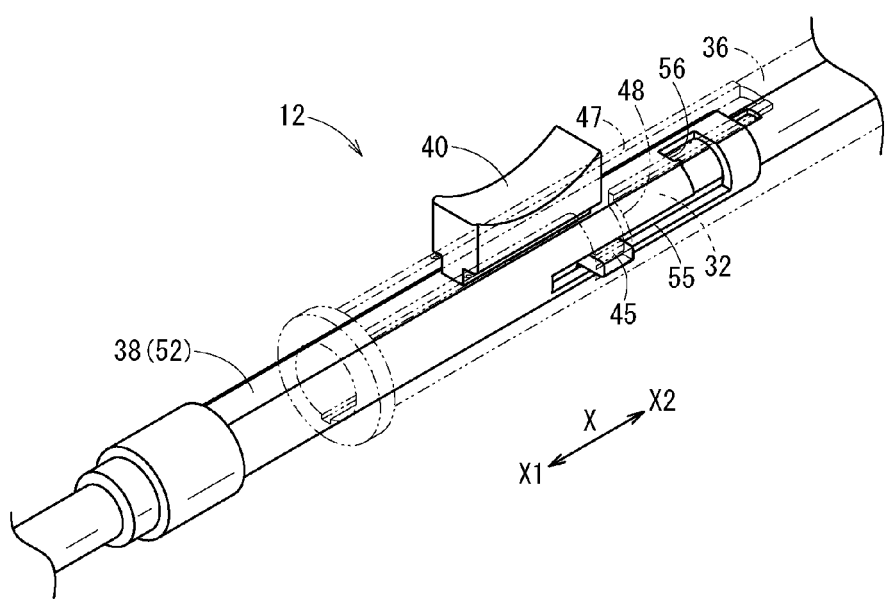
FIG. 12B is a perspective view of the handle in the medical device illustrated in FIG. 1 when the switching unit is set at the second switch position and the operating unit is at the retracted position.

Therefore, if the operating unit 40 is operated by a finger and is retracted toward the proximal end, the sheath 14 is retracted with respect to the outer basket 18 and the inner basket 20 as illustrated in FIG. 12B. At this time, as illustrated in FIG. 2, both of the outer basket 18 and the inner basket 20 are expanded in association with an exposure from the sheath 14 (expanded position of the treatment portion).

Then, the medical device 10A is operated to catch a plurality of the calculus fragments in the outer basket 18 and the inner basket 20 via gaps between the outer leg portions 19 and the inner leg portions 21. The operator then pushes the operating unit 40 toward the leading end, and the sheath 14 is advanced with respect to the outer basket 18 and the inner basket 20. Accordingly, both of the outer basket 18 and the inner basket 20 start to reduce the diameter, and grasp the plurality of calculus fragments. At this time, since the number of leg portions to be used is double compared with the case where only the outer basket 18 is used, dropping out of the calculus fragments is restricted, and the state of grasping the plurality of calculus fragments can be maintained rather easily. Subsequently, in the state of grasping the plurality of calculus fragments with the outer basket 18 and the inner basket 20, the medical device 10A is pulled out from the ureteral access sheath together with the urethroscope.

As described above, according to the medical device 10A of this embodiment, in the case of collecting large calculus fragments, the calculus fragments can be caught into the treatment portion 16 relatively easily and simply by using only one basket (only the outer basket 18). In contrast, when collecting a plurality of relatively small calculus fragments, dropping out of the plurality of small calculus fragments caught in the treatment portion 16 is restricted by using two baskets (the outer basket 18 and the inner basket 20) and increasing the number of the leg portions which constitute the treatment portion 16. Therefore, the plurality of calculus fragments can be collected more easily at one time, and an efficient medical treatment is achieved.

The medical device 10A is configured to perform a medical treatment efficiently by selecting one of the one-basket using mode in which only the outer basket 18 is used and the two-basket using mode in which both of the outer basket 18 and the inner basket 20 are used which is suitable for collecting the calculi at that position in accordance with the places of the body tissues (ureter or a renal calix) from which the calculi are to be collected.

In the case of this embodiment, the mode can be set to one of the one-basket using mode and the two-basket using mode rather easily by performing a switching operation on the switching unit 45 provided on the handle 12.

In the case of this embodiment, the switching unit 45 restricts the relative movement between the inner shaft 32 and the sliding member 38 in the axial direction and allows the relative movement between the inner shaft 32 and the gripping portion 36 in the axial direction in a state of being set to the first switch position, and restricts the relative movement between the inner shaft 32 and the gripping portion 36 in the axial direction and allows the relative movement between the inner shaft 32 and the sliding member 38 in the axial direction in a state of being set to the second switch position. In this configuration, a mechanism configured in such a manner that the inner basket 20 is always stored in the sheath 14 irrespective of the position of the sheath 14 and, in contrast, the outer basket 18 is exposed from the sheath 14 and is expanded at the time of retraction of the sheath 14 in the state in which the switching unit 45 is set to the first switch position is easily constructed.

In the case of this embodiment, the switching unit 45 restricts the relative movement between the inner shaft 32 and the sheath 14 in the axial direction by engaging the sliding member 38 at the first switch position, and hence only the outer basket 18 can reliably be expanded and contracted. Also, the switching unit 45 restricts the relative movement between the inner shaft 32 and the gripping portion 36 in the axial direction by engaging the gripping portion 36 at the second switch position, and hence both of the outer basket 18 and the inner basket 20 can reliably be expanded and contracted.

Figure 13:
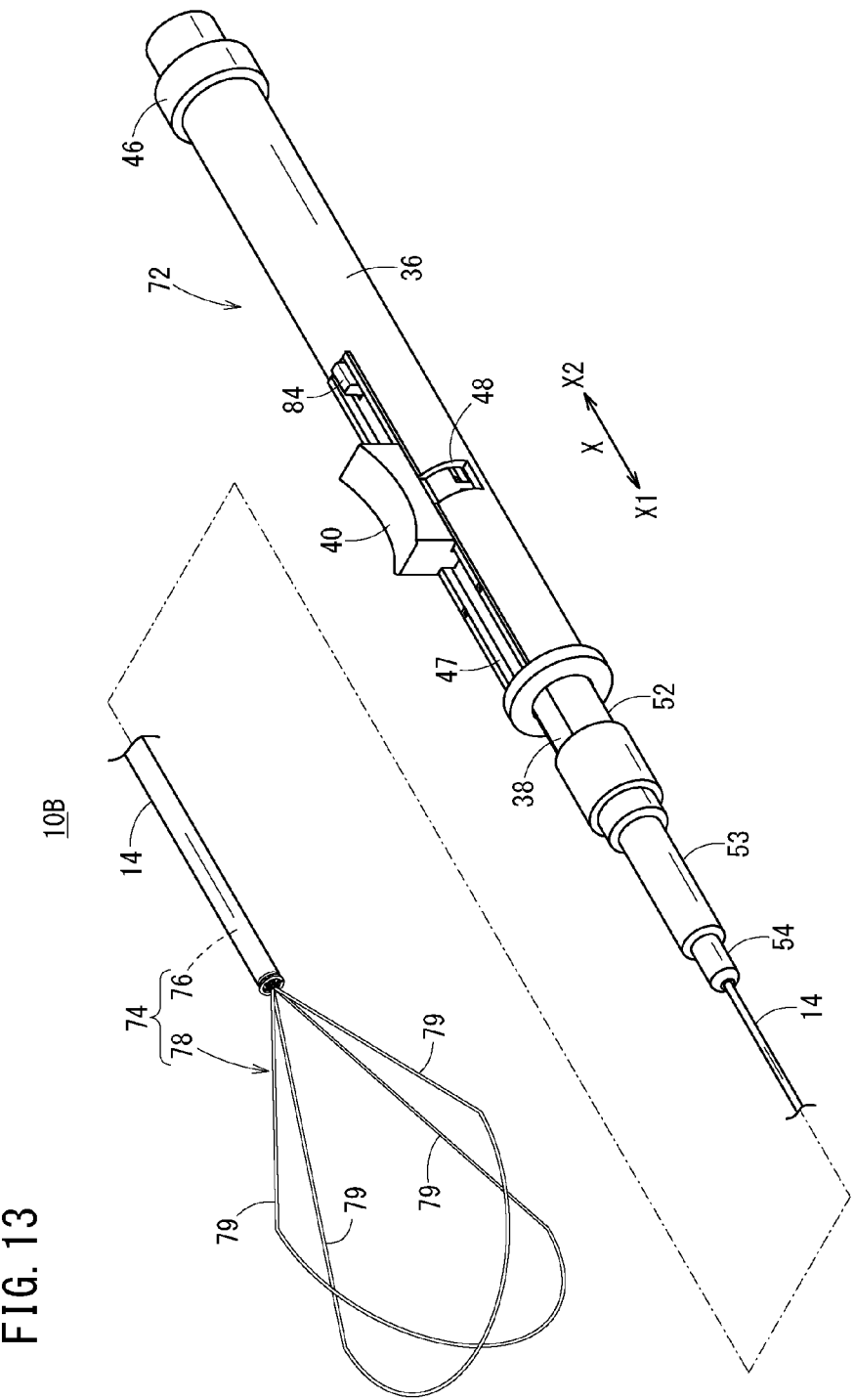
FIG. 13 is a partially omitted perspective view of a medical device (when one basket is expanded) according to a second embodiment of the present invention.

FIG. 13 is a partially omitted perspective view of a medical device 10B according to a second embodiment representing another example of the medical device disclosed here. FIG. 13 illustrates a leading end portion of the medical device 10B in an enlarged scale for the sake of easy understanding. In the medical device 10B according to the second embodiment, components having the same or similar functions and advantageous effects as the medical device 10A according to the first embodiment are denoted by the same reference signs, and a detailed description of such features is not repeated.

The medical device 10B includes a handle 72, an elongated sheath 14 extending from the handle 72, and a treatment portion 74 exposed from a leading end portion of the sheath 14 and configured to be expandable. The sheath 14 of the medical device 10B according to this embodiment is configured in the same manner as the sheath 14 of the medical device 10A according to the first embodiment.

The treatment portion 74 is configured to be stored in the sheath 14, is allowed to be exposed at least partly from the leading end portion of the sheath 14, and is configured to be contracted in the sheath 14 and expanded in association with exposure from the sheath 14. Specifically, the treatment portion 74 includes an outer basket 76 (first basket) and an inner basket 78 (second basket).

The medical device 10B is configured to be usable by switching a mode between a one-basket using mode in which only the inner basket 78 out of the outer basket 76 and the inner basket 78 is expanded and contracted and a two-basket using mode in which both the outer basket 76 and the inner basket 78 are expanded and contracted.

In other words, the outer basket 76 is configured to be stored in the sheath 14 when the inner basket 78 is expanded in front of the sheath 14 in the one-basket using mode, and is configured to expand in front of the sheath 14 together with the inner basket 78 in the two-basket using mode. FIG. 13 illustrates a state in which only the inner basket 78 is expanded.

Figure 15:
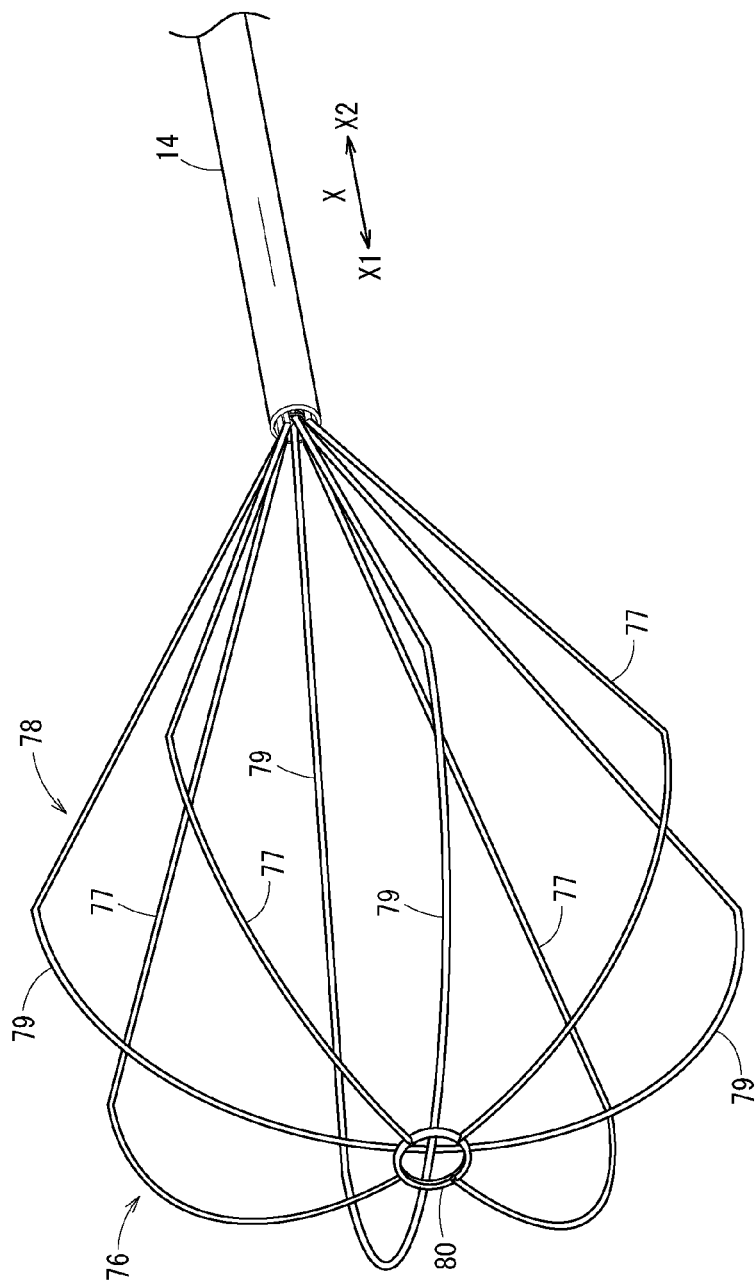
FIG. 15 is a perspective view of an outer basket and the inner basket in the medical device illustrated in FIG. 13 when being expanded.

As illustrated in FIG. 15, the outer basket 76 has a plurality of (four in this embodiment) linear outer leg portions 77 (first leg portions) disposed in a circumferential direction. Each of the outer leg portions 77 is formed of a resiliently deformable material. Therefore, the outer basket 76 presents a contracted state when stored in the sheath 14, and the respective outer leg portions 77 radially expand by their own resilient restoration force and present an expanded state when exposed from the leading end of the sheath 14.

Figure 16:
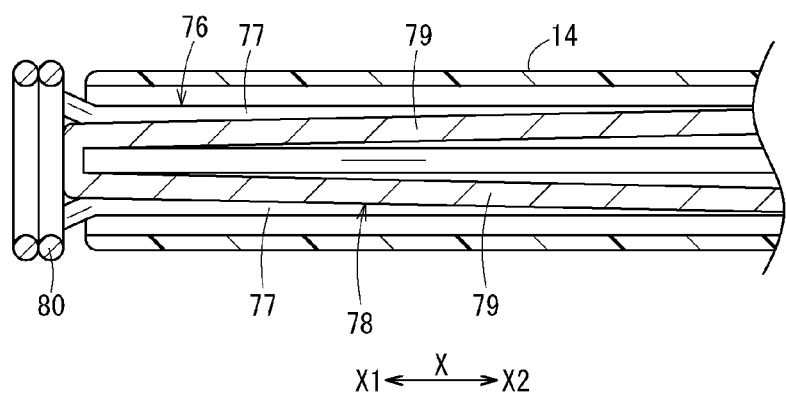
FIG. 16 is a vertical cross-sectional view of the outer basket and the inner basket when being contracted and stored in a sheath.

As illustrated in FIG. 15 and FIG. 16, the outer basket 76 includes a ring 80 coupled to the leading end portions of the plurality of outer leg portions 77. Since an outline of the ring 80 is larger than an inner diameter of a leading end opening of the sheath 14, the ring 80 is configured to engage the leading end portion of the sheath 14. The sheath 14 pushes the ring 80 toward the leading end when advancing with respect to the inner basket 78. In FIG. 16, the outer basket 76 and the inner basket 78 are stored in the sheath 14, and presents a contracted state.

Figure 14:
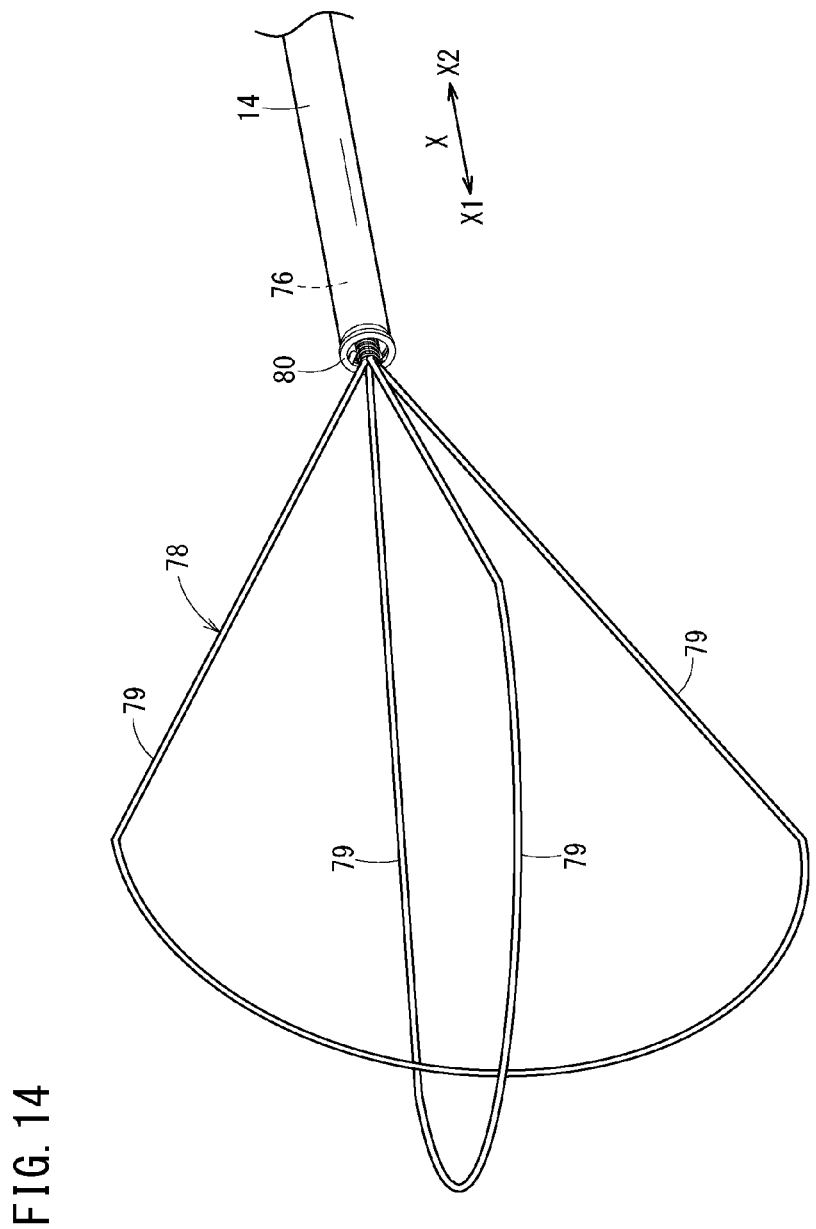
FIG. 14 is a perspective view of an inner basket in the medical device illustrated in FIG. 13 when being expanded.

As illustrated in FIG. 14, the inner basket 78 has a plurality of (four in this embodiment) linear inner leg portions 79 (second leg portions) disposed in the circumferential direction. Each of the inner leg portions 79 is formed of the resiliently deformable material. Therefore, the inner basket 78 presents a contracted state when stored in the sheath 14, and the respective inner leg portions 79 radially expand by their own resilient restoration force and present an expanded state when exposed from the leading end of the sheath 14. The inner basket 78 is configured to be exposed to the front of the sheath 14 through the ring 80 of the outer basket 76.

In the case of this embodiment, the four outer leg portions 77 radially expand at angular intervals of 90° in the circumferential direction in front view in a state in which the outer basket 76 is expanded. The four inner leg portions 79 radially expand at angular intervals of 90° in the circumferential direction in front view in a state in which the inner basket 78 is expanded. The plurality of outer leg portions 77 are arranged so as to be staggered in the circumferential direction with respect to the plurality of inner leg portions 79. The angular intervals of the outer leg portions 77 and the inner leg portions 79 adjacent in the circumferential direction are 45° in front view.

Figure 17:
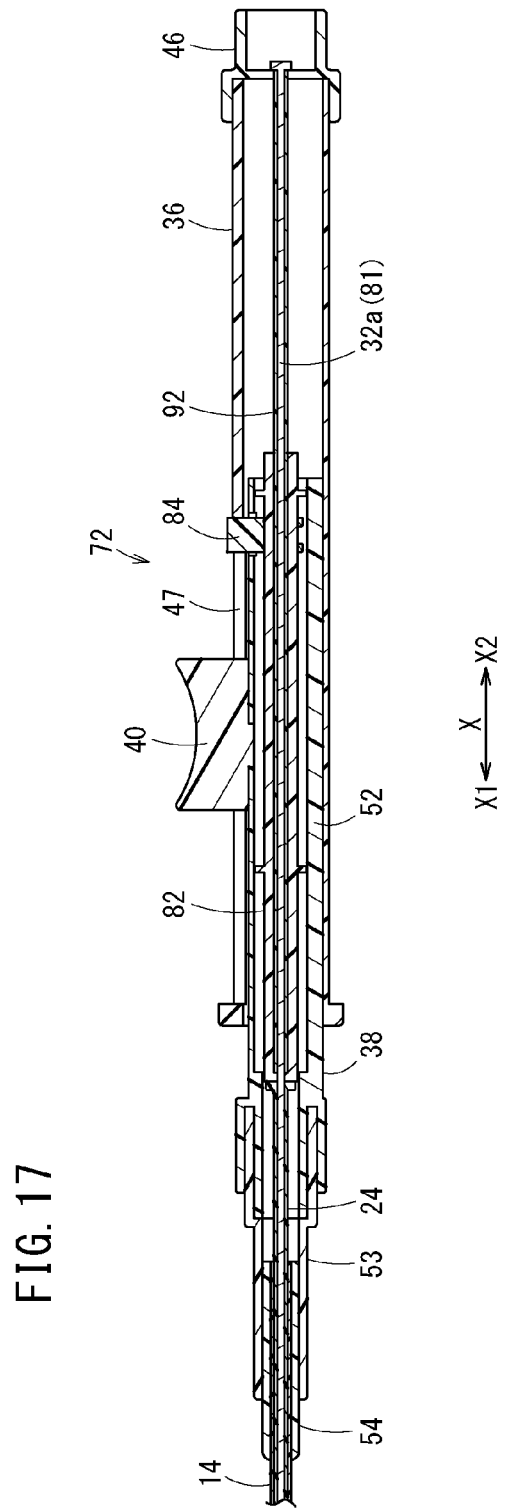
FIG. 17 is a vertical cross-sectional view of a handle of the medical device illustrated in FIG. 13.

An outer shaft 24 (see FIG. 17) extending from the outer basket 76 to the handle 72 along the sheath 14 is inserted into or positioned in the sheath 14. The outer shaft 24 is configured in the same manner as the outer shaft 24 (see FIG. 4) of the medical device 10A according to the first embodiment. An inner shaft 32a (see FIG. 17) extending from the inner basket 78 to the handle 72 along the sheath 14 is inserted into the outer shaft 24. In FIG. 17, although the inner shaft 32a is illustrated in general terms as a single linear member, the inner shaft 32a includes a plurality of longitudinally extending wires 81 extending from proximal end portions of the plurality of inner leg portions 79, which constitute the inner basket 78 toward the proximal end in the same manner as the inner shaft 32 of the medical device 10A according to the first embodiment.

As illustrated in FIG. 17, the handle 72 includes a gripping portion 36 that an operator grips, a sliding member 38 slidable in the axial direction with respect to the gripping portion 36, an operating unit 40 (operating element) provided on the sliding member 38, an outer shaft base portion 82 provided in the gripping portion 36, and a switching unit 84 rotatably supported by the outer shaft base portion 82. The gripping portion 36 and the sliding member 38 of the medical device 10B are configured in the same manner as the gripping portion 36 and the sliding member 38 of the medical device 10A according to the first embodiment, respectively.

In the medical device 10B, in a state in which the operating unit 40 is located on the leading end side of an elongated hole 47 on the gripping portion 36 (FIG. 19A and FIG. 20A), the sheath 14 coupled to the operating unit 40 via the sliding member 38 is located at an advanced position, so that both of the outer basket 76 and the inner basket 78 are stored in the sheath 14 and present a contracted state (FIG. 16). In contrast, when the operating unit 40 is retracted toward the proximal end with respect to the gripping portion 36 from this state, the sheath 14 coupled to the operating unit 40 via the sliding member 38 retracts. In association with the retracting movement of the sheath 14, a treatment portion 74 expands in front of the sheath 14. At this time, whether only the inner basket 78 expands or both of the outer basket 76 and the inner basket 78 expand is determined by a setting state (switching position) of a switching unit 84.

In FIG. 17, an outer shaft base portion 82 is arranged so as to be slidable in the axial direction within a sliding cylinder 52. As illustrated in FIG. 18, an annular rib 86 which prevents radial rattling with respect to the sliding cylinder 52 is provided on an outer peripheral portion of the outer shaft base portion 82 at a distance in the axial direction. An axial rib 88 extending in the axial direction is provided on an outer peripheral portion of the outer shaft base portion 82. In the case where the outer shaft base portion 82 is positioned at an advanced position with respect to the sliding cylinder 52, a leading end portion of the axial rib 88 enters a groove provided on an inner peripheral portion of the sliding cylinder 52 on the leading end side, so that the rotation of the outer shaft base portion 82 with respect to the sliding cylinder 52 is prevented.

The switching unit 84 is configured to be selectively switched between a first switch position (see FIG. 19A) at which only the inner basket 78 is expanded in front of the sheath 14 in association with an expanding operation of the treatment portion 74 and a second switch position (see FIG. 20A) at which both the outer basket 76 and the inner basket 78 are expanded in front of the sheath 14 in association with an expanding operation of the treatment portion 74. The switching unit 84 engages the sliding member 38 at the first switch position and engages the gripping portion 36 at the second switch position.

In the case of this embodiment, the switching unit 84 is attached to the outer shaft base portion 82 so as to be rotatable about an axial line (central axis) of the outer shaft base portion 82, and protrudes outward from the outer peripheral surface of the gripping portion 36. Specifically, the switching unit 84 includes an operation tab 90 to which a finger is placed, and a connecting portion 91 configured to be rotatably connected to the outer shaft base portion 82. The connecting portion 91 is C-shaped, and partly surrounds the outer shaft base portion 82 so as to traverse portions 88a formed by notching the axial ribs 88. Accordingly, the switching unit 84 is prevented from moving in the axial direction and is allowed to rotate with respect to the outer shaft base portion 82.

As illustrated in FIG. 17, a proximal end portion of the inner shaft 32a is fixed to a lid member 46. Therefore, the inner shaft 32a is fixed to the gripping portion 36 via the lid member 46, and a rotation and axial displacement of the inner shaft 32a with respect to the gripping portion 36 is prevented. The plurality of longitudinally extending wires 81 which constitute the inner shaft 32a are bound by a binding tube 92 over a range from a position in the vicinity of a leading end of the outer shaft base portion 82 to the lid member 46. Accordingly, rigidity of the inner shaft 32a is improved, and pushability of the inner basket 78 is secured.

The medical device 10B according to this embodiment is configured as described above, and an operation of the medical device 10B will be described below.

In the case where the medical device 10B is used, for example, for transurethral ureter lithotripsy, the calculus is fractured in the ureter into a number of calculus fragments, and then the medical device 10B is inserted into a working channel of a urethroscope in the same manner as a procedure when the medical device 10A described above is used. At the time of insertion into the urethroscope, the medical device 10B is prepared in advance to be in a state in which the outer basket 76 and the inner basket 78 are contracted in the sheath 14 by positioning the operating unit 40 on the leading end side of the elongated hole 47 of the gripping portion 36 and setting the sheath 14 at an advanced position as illustrated in FIG. 16. The medical device 10B is advanced into the ureter, and the leading end portion of the medical device 10B is moved to reach a position in the vicinity of the calculus fragments.

Figure 19A:
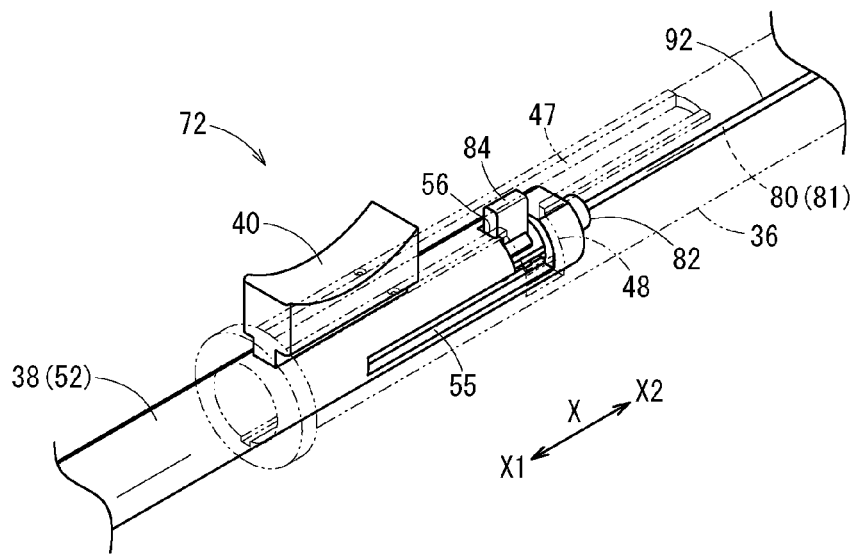
FIG. 19A is a perspective view of the handle in the medical device illustrated in FIG. 13 when the switching unit is set at a first switch position and an operating unit is at an advanced position.

Here, in the case of collecting (removing) large calculus fragments, the switching unit 84 is set to the first switch position as illustrated in FIG. 19A. In the state in which the switching unit 84 is set to the first switch position, the switching unit 84 is arranged in an engaging groove 56 of the sliding cylinder 52, and is separated from an engaging groove 48 of the gripping portion 36. Therefore, a relative movement between the outer shaft base portion 82 and the sliding member 38 in the axial direction is restricted, and the relative movement between the outer shaft base portion 82 and the gripping portion 36 in the axial direction is allowed.

Figure 19B:
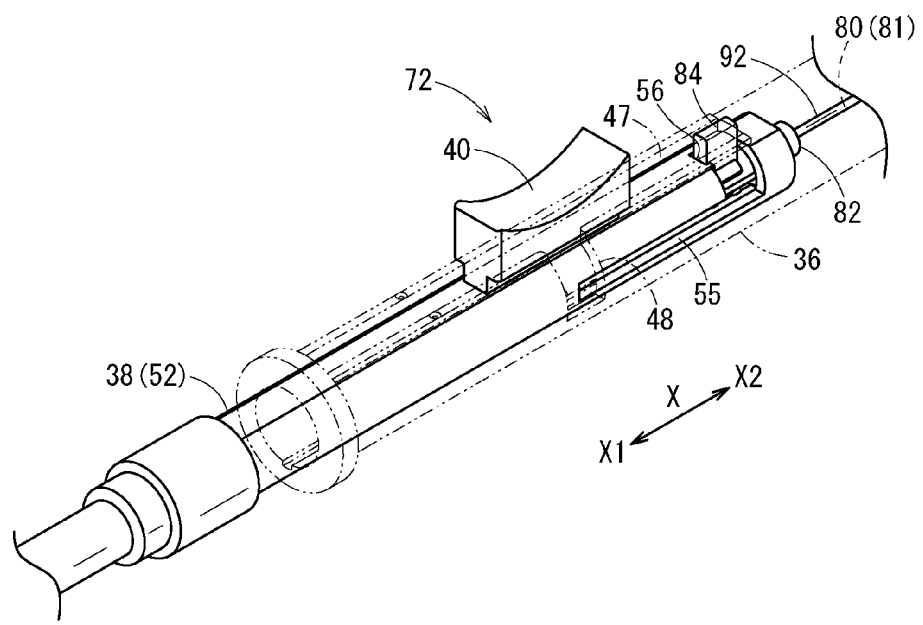
FIG. 19B is a perspective view of the handle in the medical device illustrated in FIG. 13 when the switching unit is set at the first switch position and the operating unit is at a retracted position.

Therefore, if the operating unit 40 is operated by a finger and is retracted, the sheath 14 and the outer basket 76 are integrally retracted with respect to the inner basket 78 as illustrated in FIG. 19B. At this time, as illustrated in FIG. 14, the inner basket 78 is expanded in association with exposure from the sheath 14, while the outer basket 76 remains stored in the sheath 14. Consequently, only the inner basket 78 is expanded.

Then, the medical device 10B is operated to catch the calculus fragments into the inner basket 78 via gaps among the inner leg portions 79. In this case, the basket to be used is only the inner basket 78, and since the gaps communicating an inside and an outside of the inner basket 78 (the gaps among the inner leg portions 79) are relatively large, large calculus fragments can be caught easily. When the calculus fragments are caught in the inner basket 78, the operator then pushes the operating unit 40 toward the leading end, and the sheath 14 is advanced with respect to the inner basket 78. Accordingly, the inner basket 78 starts to reduce the diameter, and grasps the calculus fragments. Subsequently, in the state of grasping the calculus fragments with the inner basket 78, the medical device 10B is pulled out from the ureteral access sheath together with the urethroscope.

Figure 20A:
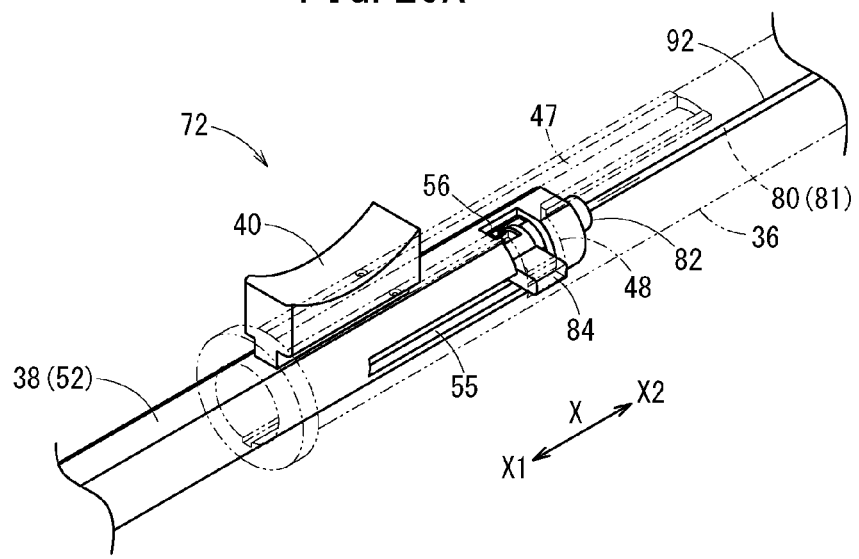
FIG. 20A is a perspective view of the handle in the medical device illustrated in FIG. 13 when the switching unit is set at a second switch position and the operating unit is at the advanced position.

In contrast, in the case of collecting (removing) a plurality of small calculus fragments, the switching unit 84 is set to the second switch position as illustrated in FIG. 20A. In the state in which the switching unit 84 is set to the second switch position, the switching unit 84 is separated from the engaging groove 56 of the sliding cylinder 52, and is positioned in the engaging groove 48 of the gripping portion 36. Therefore, a relative movement between the outer shaft base portion 82 and the sliding member 38 in the axial direction is allowed, and the relative movement between the outer shaft base portion 82 and the gripping portion 36 in the axial direction is prevented.

Figure 20B:
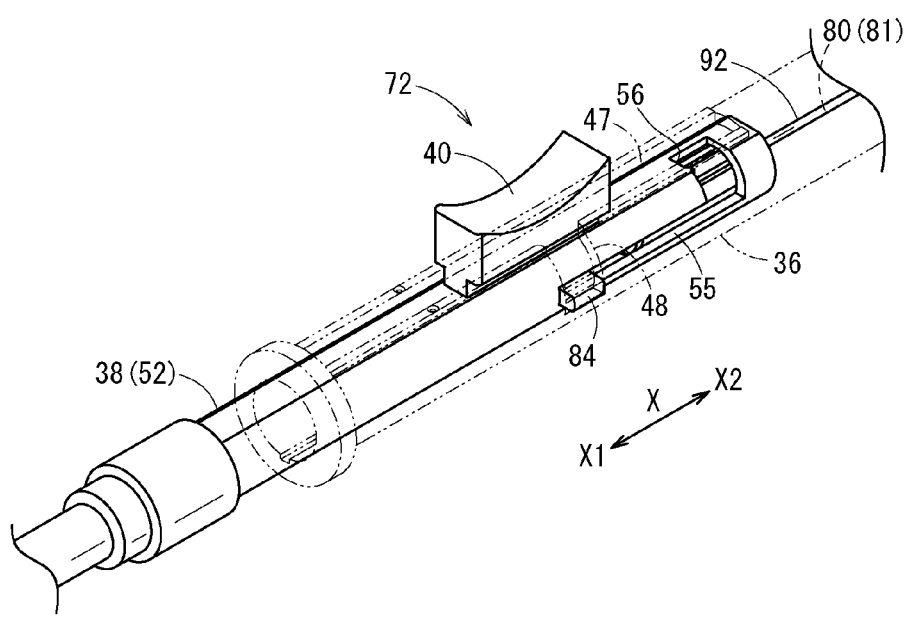
FIG. 20B is a perspective view of the handle in the medical device illustrated in FIG. 13 when the switching unit is set at the second switch position and the operating unit is at the retracted position.

Therefore, if the operating unit 40 is operated by a finger and is retracted, the sheath 14 is retracted with respect to the outer basket 76 and the inner basket 78 as illustrated in FIG. 20B. At this time, as illustrated in FIG. 15, both the outer basket 76 and the inner basket 78 are expanded in association with an exposure from the sheath 14.

Then, the medical device 10B is operated to catch the plurality of calculus fragments in the outer basket 76 and the inner basket 78 via gaps between the outer leg portions 77 and the inner leg portions 79. The operator then pushes the operating unit 40 toward the leading end, and the sheath 14 is advanced with respect to the outer basket 76 and the inner basket 78. Accordingly, both the outer basket 76 and the inner basket 78 start to reduce the diameter, and grasp a plurality of calculus fragments. At this time, since the number of leg portions to be used is double compared with the case where only the outer basket 76 is used, dropping out of the calculus fragments is restricted, and the state of grasping the plurality of calculus fragments can be maintained easily. Subsequently, in the state of grasping the plurality of calculus fragments with the outer basket 76 and the inner basket 78, the medical device 10B is pulled out from the ureteral access sheath together with the urethroscope.

As described above, according to the medical device 10B of this embodiment, in the case of collecting large calculus fragments, the calculus fragments can be caught into the treatment portion 74 relatively easily and simply by using only one basket (only the inner basket 78). In contrast, when collecting a plurality of relatively small calculus fragments, dropping out of the plurality of small calculus fragments caught in the treatment portion 74 is restricted by using two baskets (the outer basket 76 and the inner basket 78) and increasing the number of the leg portions which constitute the treatment portion 74. Therefore, the plurality of calculus fragments can be collected rather easily at the same time, and an efficient medical treatment is achieved.

In the case of this embodiment, the switching unit 84 restricts the relative movement between the outer shaft 24 and the sliding member 38 in the axial direction and allows the relative movement between the outer shaft 24 and the gripping portion 36 in the axial direction in a state of being set to the first switch position, and restricts the relative movement between the outer shaft 24 and the gripping portion 36 in the axial direction and allows the relative movement between the outer shaft 24 and the sliding member 38 in the axial direction in a state of being set to the second switch position. In this configuration, a mechanism configured in such a manner that the outer basket 76 is always stored in the sheath 14 irrespective of the position of the sheath 14 and, in contrast, the inner basket 78 is exposed from the sheath 14 and is expanded at the time of retraction of the sheath 14 in the state in which the switching unit 84 is set to the first switch position is easily constructed.

In the case of this embodiment, an axial channel and a circumferential channel which receive the switching unit 84 are formed respectively in the gripping portion 36 and the sliding member 38, and hence a configuration of switching the position of the switching unit 84 between the one-basket using mode and the two-basket using mode can be reliably structured.

In this embodiment, in the case where the calculi are harvested by using only the inner basket 78, the inner basket 78 is exposed to the front of the sheath 14 through the ring 80 coupled to the leading end portions of the plurality of outer leg portions 77 that constitute the outer basket 76, so that the expansion of the inner basket 78 is not hindered by the outer basket 76. Therefore, the inner basket 78 can be expanded without problem.

In this embodiment, when advancing the sheath 14 in order to contract the inner basket 78, the sheath 14 pushes the ring 80 of the outer basket 76 toward the leading end. Therefore, entry of the outer basket 76 to an undesirable position in the sheath 14 is effectively prevented.

Advantageous effects achieved by components of the second embodiment common to those of the first embodiment are the same as or similar to advantageous effects achieved by the common components of the first embodiment, as a matter of course.

Figure 21:
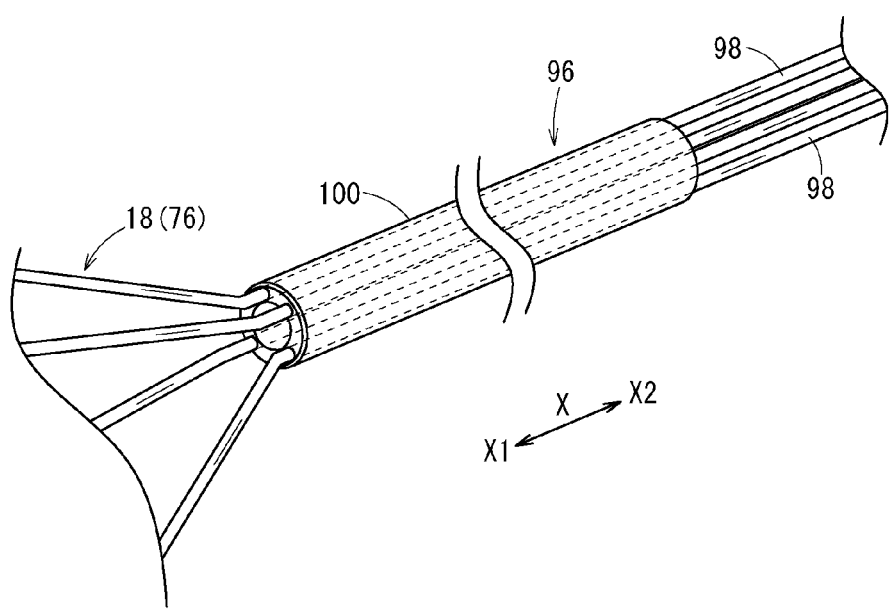
FIG. 21 is a perspective view illustrating an outer shaft according to a first modification.

In the medical devices 10A, 10B described above, an outer shaft 96 according to a first modification illustrated in FIG. 21 may be employed instead of the outer shaft 24. The outer shaft 96 includes a plurality of longitudinally extending wires 98 extending from the proximal end portion of the outer basket 18 (76) toward the proximal end and extending along the sheath 14 in the sheath 14 and a resin-made shaft tube 100 fixed to the plurality of longitudinally extending wires 98 and extending along the sheath 14 in the sheath 14. The plurality of longitudinally extending wires 98 are embedded in the shaft tube 100. A proximal end portion of the longitudinally extending wires 98 is fixed to the outer shaft base portion 42 (82).

In the configuration of the outer shaft 96 described above, the pushability of the outer basket 18 (76) may be desirably secured while restricting an increase in number of components.

Figure 22:
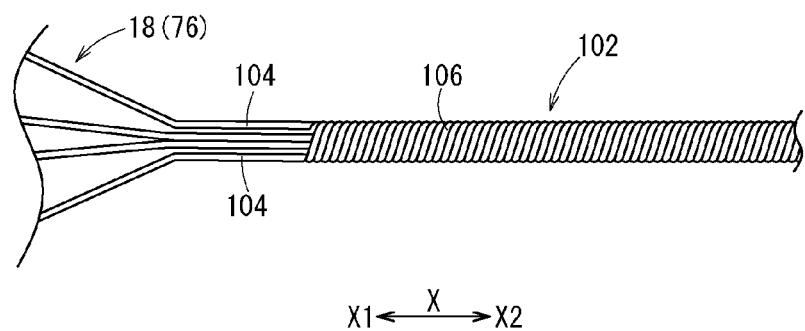
FIG. 22 is a side view illustrating an outer shaft according to a second modification.

In the medical devices 10A, 10B described above, an outer shaft 102 according to a second modification illustrated in FIG. 22 may be employed instead of the outer shaft 24. The outer shaft 102 includes a plurality of longitudinally extending wires 104 extending from the proximal end portion of the outer basket 18 (76) toward the proximal end and extending along the sheath 14 in the sheath 14. The plurality of longitudinally extending wires 104 include a coil portion 106 formed into a close coil shape over a predetermined length along the sheath 14.

In the configuration of the outer shaft 102 described above, the pushability of the outer basket 18 (76) may be desirably secured while restricting an increase in number of components.

Figure 23:
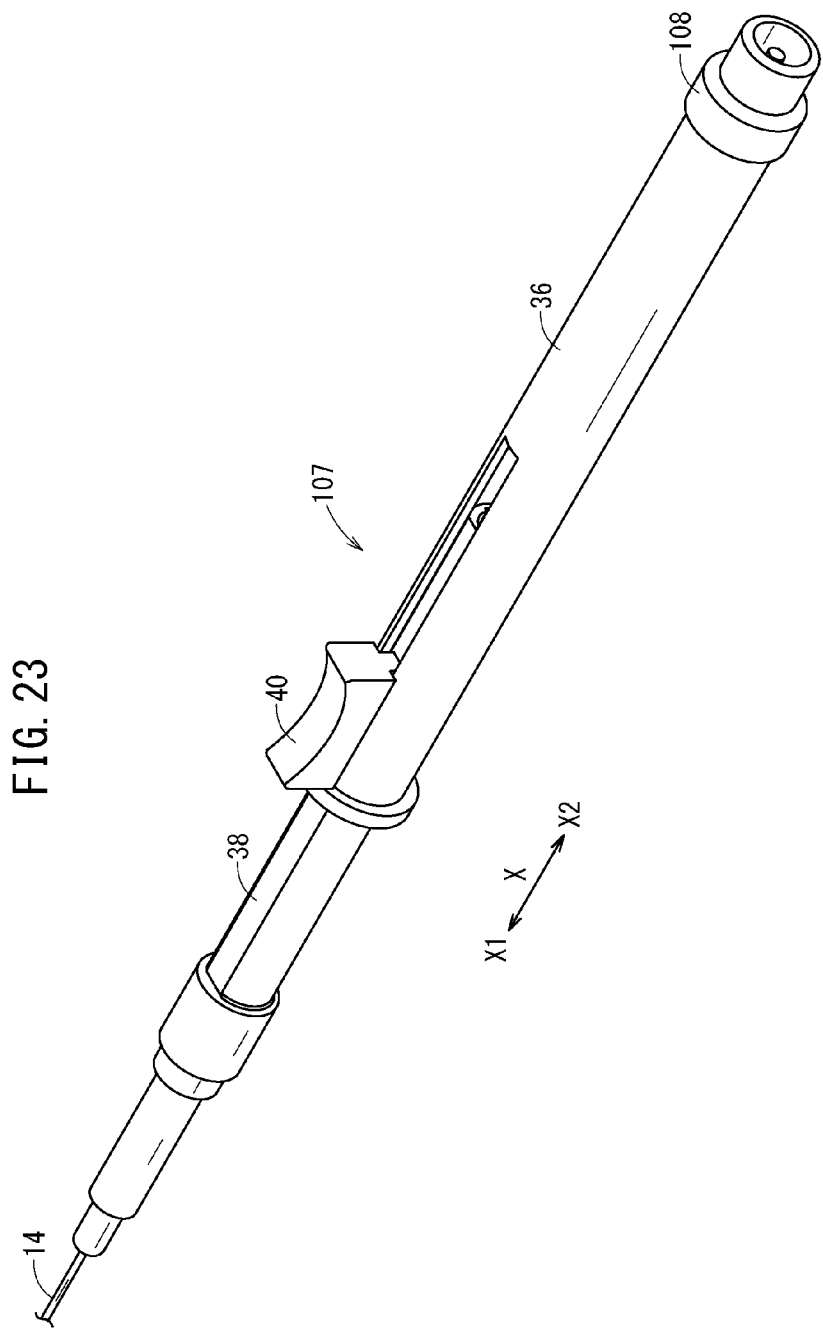
FIG. 23 is a perspective view illustrating a handle according to a modification having a switching unit provided at a proximal end of a gripping portion when viewed from a proximal end side.

In the handles 12, 72 of the embodiments described above, the tab-shaped switching units 45, 84 projecting from the outer peripheral surface of the gripping portion 36 are provided. However, as a handle 107 illustrated in FIG. 23, a cylindrical shaped switching unit 108 which is rotatable to the first switch position and the second switch position about an axial line (central axis) of the gripping portion 36 may be provided at the proximal end of the gripping portion 36.

In the embodiments described above, one of the two baskets which is not used at the beginning may be used as a substitution. In other words, in the case where the leg portions (wires) of the one used at the beginning are broken or extended and hence cannot be used any longer, the first basket is cut off and discarded and then switching operations of the switching units 45, 84, 108 are performed so that the other stored basket can be used. In this case, however, after the first basket has been discarded, the medical device cannot be used in the two-basket using mode.

The detailed description above describes embodiments of a medical device and operational method representing examples of the inventive medical device and operational method disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:
1. A medical device comprising:
a handle;
an elongated sheath extending from the handle, the elongated sheath including a part configured to be inserted into a lumen of a living body;
a treatment portion configured to contract in the sheath and expand in association with exposure outside the sheath;
the treatment portion including: a first basket having a plurality of first leg portions arranged in parallel and spaced apart from one another in a circumferential direction; and a second basket having a plurality of second leg portions arranged in parallel and spaced apart from one another in a the circumferential direction so that the plurality of second leg portions are staggered in the circumferential direction with respect to the plurality of first leg portions; and
the treatment unit being operable to: i) expand one of the first basket and the second basket in front of the sheath while the other of the first basket and the second basket remains contracted in the sheath; ii) and expand both the first and second baskets in front of the sheath together.

2. The medical device according to claim 1, wherein
the handle includes a switching unit configured to be selectively switched between a first switch position and a second switch position,
only the one of the first basket and the second basket expands in front of the sheath when the treatment portion is operated to expand in a state in which the switching unit is in the first switch position, and
both the first basket and the second basket expand in front of the sheath when the treatment portion is operated to expand in a state in which the switching unit is in the second switch position.

3. The medical device according to claim 2, comprising:
a first shaft extending from the first basket to the handle along the sheath;
a second shaft positioned in the first shaft and extending from the second basket to the handle along the sheath;
the handle including a gripping portion and a sliding member coupled to the sheath and slidable in an axial direction with respect to the gripping portion; and,
the switching unit restricting relative movement between the second shaft and the sliding member in the axial direction and allowing relative movement between the second shaft and the gripping portion in the axial direction when the switching unit is in the first switch position, and restricting relative movement between the second shaft and the gripping portion in the axial direction and allowing relative movement between the second shaft and the sliding member in the axial direction when the switching unit is in the second switch position.

4. The medical device according to claim 3, wherein:
the handle includes: a first shaft base portion arranged in the gripping portion, coupled to the first shaft and fixed to the gripping portion: and a second shaft base portion arranged in the first shaft base portion, coupled to the second shaft, and being displaceable in the axial direction with respect to the gripping portion;
the switching unit is rotatably supported by the second shaft base portion, and protrudes from an outer peripheral surface of the gripping portion,
the gripping portion includes a first axial channel configured to allow relative movement of the switching unit with respect to the gripping portion in the axial direction and a first circumferential channel configured to communicate with the first axial channel and restrict the relative movement of the switching unit with respect to the gripping portion in the axial direction by engaging the switching unit;

the sliding member includes a second axial channel configured to allow relative movement of the switching unit with respect to the sliding member in the axial direction and a second circumferential channel configured to communicate with the second axial channel and restrict the relative movement of the switching unit with respect to the sliding member in the axial direction by engaging the switching unit; and the first shaft base portion includes a third axial channel configured to allow relative movement of the switching unit with respect to the first shaft base portion in the axial direction and a third circumferential channel communicating with the third axial channel.

5. The medical device according to claim 2, comprising:
a first shaft configured to extend from the first basket to the handle along the sheath;
a second shaft positioned in the first shaft and extending from the second basket to the handle along the sheath;
the handle including a gripping portion and a sliding member that are slidable in an axial direction with respect to the gripping portion and that are coupled to the sheath;
the switching unit restricting relative movement between the first shaft and the sliding member in the axial direction and allowing relative movement between the first shaft and the gripping portion in the axial direction when the switching unit is in the first switch position, and restricting the relative movement between the first shaft and the gripping portion in the axial direction and allowing the relative movement between the first shaft and the sliding member in the axial direction when the switching unit is in the second switch position.

6. The medical device according to claim 5, wherein:
the handle includes a first shaft base portion arranged in the gripping portion, coupled to the first shaft, and displaceable in the axial direction with respect to the gripping portion;
the switching unit is rotatably supported by the first shaft base portion, and protrudes from an outer peripheral surface of the gripping portion, the gripping portion including a first axial channel configured to allow relative movement of the switching unit with respect to the gripping portion in the axial direction;
a first circumferential channel is configured to communicate with the first axial channel and restrict the relative movement of the switching unit with respect to the gripping portion in the axial direction by engaging the switching unit; and
the sliding member includes a second axial channel configured to allow relative movement of the switching unit with respect to the sliding member in the axial direction and a second circumferential channel configured to communicate with the second axial channel and restrict the relative movement of the switching unit with respect to the sliding member in the axial direction by engaging the switching unit.

7. The medical device according to claim 6, wherein:
the first basket includes a ring coupled to leading end portions of each of the plurality of first leg portions; and
the second basket is configured to be exposed in front of the sheath through the ring.

8. The medical device according to claim 7, wherein:
the ring is configured to engage a leading end portion of the sheath when the first basket is contracted inside the sheath; and
the sheath pushes the ring toward the leading end when advancing with respect to the second basket.

9. The medical device according to claim 1, comprising:
a hollow cylindrical retaining member retaining a plurality of longitudinally extending wires extending in a proximal direction from a proximal end portion of the first basket; and
a cover tube covering the longitudinally extending wires together with the retaining member and extending to the handle along the sheath and in the sheath.

10. The medical device according to claim 1, comprising:
a shaft tube fixed to a plurality of longitudinally extending wires extending in a proximal direction from a proximal end portion of the first basket and extending along the sheath and in the sheath; and
the plurality of longitudinally extending wires being embedded in the shaft tube.

11. The medical device according to claim 1, comprising:
a plurality of longitudinally extending wires extending in a proximal direction from the proximal end portion of the first basket and extending along the sheath and in the sheath; and
the plurality of longitudinally extending wires include a coil portion possessing a close coil shape over a predetermined length along the sheath.

12. The medical device according to claim 1, comprising:
an operating unit provided on the handle and configured to be operated with a finger when expanding and contracting the treatment portion; and
a tactile click response generating mechanism configured to generate a tactile click response at a position where the treatment portion comes to have a predetermined outer diameter when operating the operating unit so as to contract the treatment portion.

13. A medical device comprising:
a handle possessing a distal end;
an elongated sheath extending distally from the distal end of the handle, at least a part of the elongated sheath being configured to be inserted into a lumen of a living body;
a first basket comprised of a plurality of first leg portions arranged in parallel in a circumferential direction;
the first basket being selectively positionable inside the sheath in a contracted state and outside the sheath in an expanded state, the first basket changing between being positioned inside the sheath and being positioned outside the sheath by virtue of relative movement between the first basket and the sheath;
a second basket comprised of a plurality of second leg portions arranged in parallel in a circumferential direction, each of the second leg portions being positioned between a respective pair of circumferentially adjacent one of the inner leg portions;
the second basket being selectively positionable inside the sheath in a contracted state and outside the sheath in an expanded state, the second basket changing between being positioned inside the sheath and being positioned outside the sheath by virtue of relative movement between the second basket and the sheath;
an upstanding operating member operatively connected to the sheath and manually-operable to axially move the sheath; and
an upstanding switch that is manually-operable to switch between a first switch position in which operation of the operating member axially moves the sheath and the second basket in the proximal direction relative to the first basket so that the first basket is positioned outside the sheath in the expanded state while the second basket is positioned inside the sheath in the contracted state, and a second switch position in which operation of the operating member axially moves the sheath in the proximal direction relative to both the first basket and the second basket so that both the first basket and the second basket are positioned outside the sheath in the expanded state.

14. The medical device according to claim 13, further comprising:
- a first shaft extending from the first basket and along the sheath;
- a second shaft positioned in the first shaft and extending from the second basket along the sheath; and
- the handle including a gripping portion and a sliding member coupled to the sheath and slidable in an axial direction with respect to the gripping portion.

15. The medical device according to claim 14, wherein the handle includes: a first shaft base portion arranged in the gripping portion, coupled to the first shaft and fixed to the gripping portion; and a second shaft base portion arranged in the first shaft base portion, coupled to the second shaft, and being displaceable in the axial direction with respect to the gripping portion.

* * * * *